(12) United States Patent
Tezel et al.

(10) Patent No.: US 9,155,790 B2
(45) Date of Patent: Oct. 13, 2015

(54) METHODS AND COMPOSITIONS FOR MODULATING OCULAR DAMAGE

(75) Inventors: Tongalp H. Tezel, Louisville, KY (US); Henry J. Kaplan, Louisville, KY (US); Robert A. Mitchell, Louisville, KY (US); John O. Trent, Louisville, KY (US)

(73) Assignee: University of Lousiville Research Foundation, Inc., Louisville, KY (US)

( * ) Notice: Subject to any disclaimer, the term of this patent is extended or adjusted under 35 U.S.C. 154(b) by 192 days.

(21) Appl. No.: 13/698,518

(22) PCT Filed: May 20, 2011

(86) PCT No.: PCT/US2011/037320
§ 371 (c)(1),
(2), (4) Date: Mar. 22, 2013

(87) PCT Pub. No.: WO2011/146824
PCT Pub. Date: Nov. 24, 2011

(65) Prior Publication Data
US 2013/0177552 A1 Jul. 11, 2013

Related U.S. Application Data

(60) Provisional application No. 61/396,009, filed on May 20, 2010, provisional application No. 61/419,404, filed on Dec. 3, 2010, provisional application No. 61/480,731, filed on Apr. 29, 2011.

(51) Int. Cl.
*A61K 31/517* (2006.01)
*A61K 39/395* (2006.01)
*A61K 31/505* (2006.01)
*A61K 31/53* (2006.01)
*A61K 45/06* (2006.01)

(52) U.S. Cl.
CPC ........... *A61K 39/3955* (2013.01); *A61K 31/505* (2013.01); *A61K 31/53* (2013.01); *A61K 45/06* (2013.01)

(58) Field of Classification Search
USPC ........................................................ 514/256
See application file for complete search history.

(56) References Cited

U.S. PATENT DOCUMENTS

| 7,517,523 | B2 | 4/2009 | Bucala et al. |
| 7,863,313 | B2 | 1/2011 | Morand et al. |
| 8,293,891 | B2 | 10/2012 | Dorsch et al. |
| 2003/0187007 | A1 | 10/2003 | Cao et al. |
| 2005/0130954 | A1 | 6/2005 | Mitchell et al. |
| 2005/0196795 | A1 | 9/2005 | Siegler et al. |
| 2007/0281924 | A1 | 12/2007 | Gaeta |
| 2008/0317759 | A1 | 12/2008 | Bucala et al. |
| 2011/0009412 | A1 | 1/2011 | Mitchell et al. |
| 2012/0157521 | A1* | 6/2012 | Kremmidiotis ............... 514/469 |
| 2013/0079361 | A1* | 3/2013 | Mitchell et al. ............... 514/274 |

FOREIGN PATENT DOCUMENTS

| EP | 0 767 170 | 4/1997 |
| WO | WO01/07436 | 2/2001 |
| WO | WO 02/079197 | 10/2002 |
| WO | WO 2005/016914 | 2/2005 |
| WO | WO 2005/121106 | 12/2005 |
| WO | WO2006/005914 | 1/2006 |
| WO | WO2007140263 | * 12/2007 |
| WO | WO 2008/099000 | 8/2008 |
| WO | WO 2011/038234 | 3/2011 |

OTHER PUBLICATIONS

Al Abed et al. (2005). ISO-1 binding to the tautomerase active site of MIF inhibits its pro-inflammatory activity and increases survival in severe sepsis. J Biol Chem. 280:36541-36544.
Altenbach et al., "Structure-Activity Studies on a Series of a 2-Aminopyrimidine-Containing Histamine H4 Receptor Ligands," Journal of Medicinal Chemistry, Vol. 51, No. 20, pp. 6571-6580 (Jan. 1, 2008).
Babu et al., Synthesis, Antitumor and Antibacterial Activities of Certain Substituted Pyrimidines Bearing Benzofuran Indian Journal of Pharmaceutical Sciences, vol. 66, No. 5, pp. 647-652 (2004).
Bando et al. (2002). Expression of macrophage migration inhibitory factor in human breast cancer: association with nodal spread. Jpn. J. Cancer Res. 93:389-396.
Bochot et al. (2002) Intravitreal delivery of oligonucleotides by sterically stabilized liposomes. Invest. Ophthalmol. Vis. Sci. 43:253-259.
Bourges et al. (2003) Ocular drug delivery targeting the retina and retinal pigment epithelium using polylactide nanoparticles. Invest. Ophthalmol. Vis. Sci. 44:3562-3569.
Brown, J.M. (1993). SR 4233 (tirapazamine): a new anticancer drug exploiting hypoxia in solid tumours. British Journal of Cancer. 67:1163-1170.
Bucala (1996). MIF rediscovered: cytokine, pituitary hormone, and glucocorticoid-induced regulator of the immune response. FASEB J. 14:1607-1613.
CAS Registration No. 39189-98-5 (Entered Nov. 16, 1984).
Chesney et al. (1999). An essential role for macrophage migration inhibitory factor (MIF) in angiogenesis and the growth of a murine lymphoma. Mol. Med. 5:181-191.

(Continued)

*Primary Examiner* — Rei-Tsang Shiao
(74) *Attorney, Agent, or Firm* — Jenkins, Wilson, Taylor & Hunt, P.A.

(57) ABSTRACT

Methods for modulating eye damage associated with a disease or disorder, and/or damage incident to trauma including but not limited to trauma associated with ocular surgery are provided. In some embodiments, the methods include administering an effective amount of a modulator of a migration inhibitory factor (MIF) polypeptide biological activity to a subject. Also provided are methods for modulating the severity of delaying the onset of and/or inhibiting and/or preventing the development of an ocular disease, and methods for modulating the severity of delaying the onset of and/or inhibiting and/or preventing the development of scarring and/or other consequence of wound healing incident to ocular surgery, as well as modulating the survival, function, and/or differentiation of engrafted cells that can be employed as part of tissue engineering procedures to correct structural, functional, and/or cellular defects of the eye.

13 Claims, 17 Drawing Sheets

(56) References Cited

OTHER PUBLICATIONS del Vecchio et al. (2000). Macrophage migration inhibitory factor in prostatic adenocarcinoma: correlation with tumor grading and combination endocrine treatment-related changes. Prostate. 45:51-57.
Dios et al. (2002). Inhibition of MIF bioactivity by rational design of pharmacological inhibitors of MIF tautomerase activity. J Med. Chem. 45:2410-2416.
European Search Report corresponding to European Patent Application No. 10819534.8-1452/12480235 dated Apr. 8, 2013.
Fingerle-Rowson et al. (2003). The p53-dependent effects of macrophage migration inhibitory factor revealed by gene targeting. Proc. Natl. Acad.Sci. U.S. A 100: 9354-9359.
Hira et al. (2005). Overexpression of macrophage migration inhibitory factor induces angiogenesis and deteriorates prognosis after radical resection for hepatocellular carcinoma. Cancer. 103:588-598.
International Preliminary Report on Patentability corresponding to International Application No. PCT/US2007/069672 dated Nov. 28, 2008.
International Search Report corresponding to International Application No. PCT/US2007/069672, dated Aug. 7, 2008.
Kamimura et al. (2000). Intracellular distribution of macrophage migration inhibitory factor predicts the prognosis of patients with adenocarcinoma of the lung. Cancer. 89:334-341.
Koong et al. (2000a). Candidate Genes for the Hypoxic Tumor Phenotype. Cancer Res. 60:883-887.
Koong, et al. (2000b). Pancreatic tumors show high levels of hypoxia Int. J Radiat. Oncol. Bioi Phys. 48:919-922.
Liao et al. (2003). Adhesion-dependent Signaling by Macrophage Migration Inhibitory Factor (MIF). J Bioi Chem. 278:76-81.
Markert et al. (2001). Differential gene expression profiling in human brain tumors. Physiol Genomics. 5, 21-33.
Matsuda et al. (1997). Expression of Macrophage Migration Inhibitory Factor in Corneal Wound Healing in Rats. Invest. Ophthalmol. Vis. Sci. 38:1555-1562.
Matsunaga et al. (1999). Enzyme activity of macrophage migration inhibitory factor toward oxidized catecholamines. J. Biol. Chem. 274:3268-3271.
McInnes et al. (1988). Interleukin 4 induces cultured monocytes/macrophages to form giant multinucleated cells. J. Exp. Med. 167:598-611.
Meyer-Siegler et al. (2002). Macrophage migration inhibitory factor evaluation compared with prostate specific antigen as a biomarker in patients with prostate carcinoma. Cancer. 94:1449-456.
Meyer-Siegler et al. (2005). Further evidence for increased macrophase migration inhibitory factor expression in prostate cancer, BMC Cancer, vol. 5, No. 1, p. 73 (Jul. 6, 2005).
Meyer-Siegler et al. (2006). Inhibition of macrophage migration inhibitory factor or its receptor (CD74) attenuates growth and invasion of DU-145 prostate cancer cells. J Immunol. 177:8730-8739.
Mitchell et al. (1999). Sustained mitogen-activated protein kinase (MAPK) and cytoplasmic phospholipase A2 activation by macrophage migration inhibitory factor (MIF). Regulatory role in cell proliferation and glucocorticoid action. J Bioi Chem. 274:18100-18106.
Mitchell et al. (2002). Macrophage migration inhibitory factor (MIF) sustains macrophage proinflammatory function by inhibiting p53: regulatory role in the innate immune response. Proc. Natl. Acad. Sci. USA. 99:345-350.
Nicoletti et al. (2005). Macrophage migration inhibitory factor (MIF) seems crucially involved in Guillain-Barré syndrome and experimental allergic neuritis. J Neuroimmunol. 168:168-174.
Nimavat et al., Synthesis, anticancer, antitubercular and antimicrobial activity of 1-substituted 3-aryl-5-(3'-bromophenyl)-pyrazolines. Indian Journal of Heterocyclic Chemistry, vol. 12, No. 3, pp. 217-220 (2003).
Notice of Acceptance corresponding to Australian Patent Application No. AU2007267593 dated Mar. 21, 2013.
Notification Concerning Transmittal of International Preliminary Report on Patentability corresponding to International Application No. PCT/US2011/037320 dated Nov. 29, 2012.
Notification of Transmittal of International Search Report and the Written Opinion of the International Searching Authority, or the Declaration corresponding to International Application No. PCT/US10/50206 dated Mar. 29, 2012.
Notification of Transmittal of International Search Report and the Written Opinion of the International Searching Authority, or the Declaration corresponding to International Application No. PCT/US2011/037320 dated Oct. 21, 2011.
Office Action corresponding to Chinese Patent Application 200780028307 dated Nov. 8, 2011.
Office Action corresponding to Japanese Patent Application No. 2009-513395 dated Sep. 7, 2012.
Office Action corresponding to U.S. Appl. No. 12/301,783 dated Dec. 20, 2012.
Office Action corresponding to U.S. Appl. No. 12/301,783 dated Sep. 6, 2012.
Office Action Corresponding to U.S. Appl. No. 13/498,036 dated May 14, 2013.
Ogawa et al., "An antibody for Macrophase Migration Inhibitory Factor Suppresses Tumour Growth and Inhibits Tumour-Associated Angiogensis," Cytokine, vol. 12, No. 4, pp. 309-314 (2000).
Orita et al. (2001). Coumarin and chromen-4-one analogues as tautomerase inhibitors of macrophage migration inhibitory factor: discovery and X-ray crystallography. J Med. Chem. 44:540-547.
Ouertatani-Sakouhi et al. (2010). Kinetic-based high-throughput screening assay to discover novel classes of macrophase migration inhibitory factor inhibitors. J. Biomol. Screen. 15:347-358.
Petrenko & Moll (2005). Macrophage migration inhibitory factor MIF interferes with the Rb-E2F pathway. Mol. Cell. 17:225-236.
Pozzi et al. (1992). Human recombinant migration inhibitory factor activates human macrophages to kill tumor cells. Cellular Immunol. 145:372-379.
Ren et al. (2005). Macrophage migration inhibitory factor stimulates angiogenic factor expression and correlates with differentiation and lymph node status in patients with esophageal squamous cell carcinoma. Ann. Surg. 242:55-63.
Ren et al. (2006). Inhibition of tumor growth and metastasis in vitro and in vivo by targeting macrophage migration inhibitory factor in human neuroblastoma. Oncogene. 25(25):3501-8.
Rendon et al. (2007). Regulation of human lung adenocarcinoma cell migration and invasion by MIF: Role of Rac1 GTPase and lipid raft assembly. J Biol Chem. 282(41):29910-8.
Senter et al. (2002). Inhibition of macrophage migration inhibitory factor (MIF) tautomerase and biological activities by acetaminophen metabolites. Proc. Natl. Acad. Sci. USA. 99:144-149.
Suzuki et al., "Structure-activity relationships of pyrazine-based CK2 inhibitors: Synthesis and evaluation of 2,6-disubstituted pyrazines and 4,6-disubstituted pyrimidines," Archiv Der Pharmazie, vol. 341, No. 9, pp. 554-561 (Sep. 1, 2008).
Wang et al. (2009) Autophagy and exosomes in the aged retinal pigment epithelium: possible relevance to drusen formation and age-related macular degeneration. PLoS One. 4:1-13.
Wilson et al. (2005). Macrophage migration inhibitory factor promotes intestinal tumorigenesis. Gastroenterology. 129:1485-1503.
Winner et al. (2008). A novel, macrophage migration inhibitory factor suicide substrate inhibits motility and growth of lung cancer cells. 68:7253-7257.
Wistow et al. (1993). A macrophage migration inhibitory factor is expressed in the differentiating cells of the eye lens. Proc. Natl. Acad. Sci. USA. 90:1272-1275.
Zhong & Bowen (2006). Antiangiogenesis drug design: multiple pathways targeting tumor vasculature. Curr. Med. Chem. 13:849-862.
Extended European Search Report corresponding to European Patent Application No. 07811937.7 dated Jun. 17, 2013.
Notice of Allowance corresponding to U.S. Appl. No. 12/301,783 dated Nov. 28, 2014.
Official Action corresponding to European Patent Application No. 07 811 937.7-1460 dated Mar. 18, 2014.
Official Action corresponding to European Patent Application No. 10 819 534.8-1452 dated Jun. 20, 2014.
Official Action corresponding to U.S. Appl. No. 12/301,783 dated Apr. 1, 2014.
Official Action corresponding to U.S. Appl. No. 13/498,036 dated Apr. 24, 2014.
Official Action corresponding to U.S. Appl. No. 13/498,036 dated Oct. 27, 2014.
Official Action corresponding to U.S. Appl. No. 13/498,036 dated Oct. 4, 2013.
STN CAS RN: 1049024-02-03 (entered Sep. 12, 2008).

* cited by examiner

RPE65 STAIN

SEQUENCE LISTING

```
<160> NUMBER OF SEQ ID NOS: 26

<210> SEQ ID NO 1
<211> LENGTH: 561
<212> TYPE: DNA
<213> ORGANISM: Homo sapiens
<220> FEATURE:
<221> NAME/KEY: CDS
<222> LOCATION: (98)..(445)

<400> SEQUENCE: 1
accacagtgg tgtccgagaa gtcaggcacg tagctcagcg gcggccgcgg cgcgtgcgtc      60
tgtgcctctg cgcgggtctc ctggtccttc tgccatc atg ccg atg ttc atc gta     115
                                        Met Pro Met Phe Ile Val
                                         1               5 aac acc aac gtg ccc cgc gcc tcc gtg ccg gac ggg ttc ctc tcc gag     163
Asn Thr Asn Val Pro Arg Ala Ser Val Pro Asp Gly Phe Leu Ser Glu
             10                  15                  20 ctc acc cag cag ctg gcg cag gcc acc ggc aag ccc ccc cag tac atc     211
Leu Thr Gln Gln Leu Ala Gln Ala Thr Gly Lys Pro Pro Gln Tyr Ile
         25                  30                  35 gcg gtg cac gtg gtc ccg gac cag ctc atg gcc ttc ggc ggc tcc agc     259
Ala Val His Val Val Pro Asp Gln Leu Met Ala Phe Gly Gly Ser Ser
     40                  45                  50 gag ccg tgc gcg ctc tgc agc ctg cac agc atc ggc aag atc ggc ggc     307
Glu Pro Cys Ala Leu Cys Ser Leu His Ser Ile Gly Lys Ile Gly Gly
 55                  60                  65                  70 gcg cag aac cgc tcc tac agc aag ctg ctg tgc ggc ctg ctg gcc gag     355
Ala Gln Asn Arg Ser Tyr Ser Lys Leu Leu Cys Gly Leu Leu Ala Glu
                 75                  80                  85 cgc ctg cgc atc agc ccg gac agg gtc tac atc aac tat tac gac atg     403
Arg Leu Arg Ile Ser Pro Asp Arg Val Tyr Ile Asn Tyr Tyr Asp Met
             90                  95                 100 aac gcg gcc aat gtg ggc tgg aac aac tcc acc ttc gcc taa             445
Asn Ala Ala Asn Val Gly Trp Asn Asn Ser Thr Phe Ala
        105                 110                 115 gagccgcagg gacccacgct gtctgcgctg gctccacccg ggaacccgcc gcacgctgtg    505
```

```
ttctaggccc gcccacccca accttctggt ggggagaaat aaacggttta gagact        561
```

<210> SEQ ID NO 2
<211> LENGTH: 115
<212> TYPE: PRT
<213> ORGANISM: Homo sapiens

<400> SEQUENCE: 2

```
Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
            100                 105                 110

Thr Phe Ala
        115
```

<210> SEQ ID NO 3
<211> LENGTH: 19
<212> TYPE: DNA
<213> ORGANISM: Homo sapiens

<400> SEQUENCE: 3

```
gttcatcgta aacaccaac                                                 19
```

<210> SEQ ID NO 4
<211> LENGTH: 19
<212> TYPE: DNA
<213> ORGANISM: Homo sapiens

<400> SEQUENCE: 4

```
catcgtaaac accaacgtg                                                 19
```

<210> SEQ ID NO 5
<211> LENGTH: 19
<212> TYPE: DNA
<213> ORGANISM: Homo sapiens

<400> SEQUENCE: 5

```
tcgtaaacac caacgtgcc                                                 19
```

<210> SEQ ID NO 6
<211> LENGTH: 19
<212> TYPE: DNA
<213> ORGANISM: Homo sapiens

<400> SEQUENCE: 6

```
cgtaaacacc aacgtgccc                                                 19
```

<210> SEQ ID NO 7
<211> LENGTH: 19
<212> TYPE: DNA

```
<213> ORGANISM: Homo sapiens

<400> SEQUENCE: 7
ggttcctctc cgagctcac                                                    19

<210> SEQ ID NO 8
<211> LENGTH: 19
<212> TYPE: DNA
<213> ORGANISM: Homo sapiens

<400> SEQUENCE: 8
acatcgcggt gcacgtggt                                                    19

<210> SEQ ID NO 9
<211> LENGTH: 19
<212> TYPE: DNA
<213> ORGANISM: Homo sapiens

<400> SEQUENCE: 9
ggaccagctc atggccttc                                                    19

<210> SEQ ID NO 10
<211> LENGTH: 19
<212> TYPE: DNA
<213> ORGANISM: Homo sapiens

<400> SEQUENCE: 10
gcctgcacag catcggcaa                                                    19

<210> SEQ ID NO 11
<211> LENGTH: 19
<212> TYPE: DNA
<213> ORGANISM: Homo sapiens

<400> SEQUENCE: 11
cctgcacagc atcggcaag                                                    19

<210> SEQ ID NO 12
<211> LENGTH: 19
<212> TYPE: DNA
<213> ORGANISM: Homo sapiens

<400> SEQUENCE: 12
ctgcacagca tcggcaaga                                                    19

<210> SEQ ID NO 13
<211> LENGTH: 19
<212> TYPE: DNA
<213> ORGANISM: Homo sapiens

<400> SEQUENCE: 13
gcgcagaacc gctcctaca                                                    19

<210> SEQ ID NO 14
<211> LENGTH: 19
<212> TYPE: DNA
<213> ORGANISM: Homo sapiens

<400> SEQUENCE: 14
cagaaccgct cctacagca                                                    19

<210> SEQ ID NO 15
<211> LENGTH: 19
```

```
<212> TYPE: DNA
<213> ORGANISM: Homo sapiens

<400> SEQUENCE: 15
agaaccgctc ctacagcaa                                                19

<210> SEQ ID NO 16
<211> LENGTH: 19
<212> TYPE: DNA
<213> ORGANISM: Homo sapiens

<400> SEQUENCE: 16
tctacatcaa ctattacga                                                19

<210> SEQ ID NO 17
<211> LENGTH: 19
<212> TYPE: DNA
<213> ORGANISM: Homo sapiens

<400> SEQUENCE: 17
ctacatcaac tattacgac                                                19

<210> SEQ ID NO 18
<211> LENGTH: 19
<212> TYPE: DNA
<213> ORGANISM: Homo sapiens

<400> SEQUENCE: 18
tacatcaact attacgaca                                                19

<210> SEQ ID NO 19
<211> LENGTH: 19
<212> TYPE: DNA
<213> ORGANISM: Homo sapiens

<400> SEQUENCE: 19
acatcaacta ttacgacat                                                19

<210> SEQ ID NO 20
<211> LENGTH: 19
<212> TYPE: DNA
<213> ORGANISM: Homo sapiens

<400> SEQUENCE: 20
catcaactat tacgacatg                                                19

<210> SEQ ID NO 21
<211> LENGTH: 19
<212> TYPE: DNA
<213> ORGANISM: Homo sapiens

<400> SEQUENCE: 21
tcaactatta cgacatgaa                                                19

<210> SEQ ID NO 22
<211> LENGTH: 19
<212> TYPE: DNA
<213> ORGANISM: Homo sapiens

<400> SEQUENCE: 22
caactattac gacatgaac                                                19

<210> SEQ ID NO 23
```

```
<211> LENGTH: 19
<212> TYPE: DNA
<213> ORGANISM: Homo sapiens

<400> SEQUENCE: 23
actattacga catgaacgc                                                19

<210> SEQ ID NO 24
<211> LENGTH: 19
<212> TYPE: DNA
<213> ORGANISM: Homo sapiens

<400> SEQUENCE: 24
acaactccac cttcgccta                                                19

<210> SEQ ID NO 25
<211> LENGTH: 19
<212> TYPE: DNA
<213> ORGANISM: Homo sapiens

<400> SEQUENCE: 25
caactccacc ttcgcctaa                                                19

<210> SEQ ID NO 26
<211> LENGTH: 19
<212> TYPE: DNA
<213> ORGANISM: Homo sapiens

<400> SEQUENCE: 26
ccttctggtg gggagaaat                                                19
```

METHODS AND COMPOSITIONS FOR MODULATING OCULAR DAMAGE

CROSS-REFERENCE TO RELATED APPLICATIONS

The presently disclosed subject matter claims the benefit of U.S. Provisional Patent Application Ser. No. 61/396,009, filed May 20, 2010; U.S. Provisional Patent Application Ser. No. 61/419,404, filed Dec. 3, 2010; and U.S. Provisional Patent Application Ser. No. 61/480,731, filed Apr. 29, 2011. The disclosure of each of these U.S. Provisional Patent Applications is incorporated herein by reference in its entirety.

GOVERNMENT INTEREST

This invention was made with U.S. government support under grant number 5P20RR018733 awarded by the Centers of Biomedical Research Excellence of the National Institutes of Health (NIH) of the United States of America, and by grant number R24EY015636 from the NIH. The Government of the United States of America has certain rights in the invention.

REFERENCE TO SEQUENCE LISTING

The Sequence Listing associated with the instant disclosure has been electronically submitted to the United States Patent and Trademark Office as International Receiving Office as an eight (8) kilobyte ASCII text file entitled "1577_31PCT_ST25.txt" and created on Mar. 25, 2011. The Sequence Listing submitted via EFS-Web is hereby incorporated by reference in its entirety.

TECHNICAL FIELD

The presently disclosed subject matter relates to methods and compositions for modulating or preventing ocular damage. In some embodiments, the presently disclosed subject matter relates to methods for modulating or preventing eye damage associated with a disease or disorder, and/or damage incident to ocular surgery, the method comprising administering to a subject an effective amount of a modulator of a macrophage migration inhibitory factor (MIF) polypeptide biological activity.

BACKGROUND

Disorders of and injuries to the eyes are a significant health concern, particular as the population ages. Major ocular disorders are known to affect the retina, the lens, and/or the cornea of the eyes. Among the most important retinal disorders are macular holes and degeneration, retinal tears, and diabetic retinopathy, to name but a few.

Various ocular disorders are associated with cellular processes such as, but not limited to cellular proliferation, survival, migration, differentiation, and angiogenesis. For example, macular degeneration results from loss of photoreceptors in the portion of the central retina, termed the macula, which is responsible for high-acuity vision. Degeneration of the macula is associated with abnormal deposition of extracellular matrix components in the membrane between the retinal pigment epithelium (RPE) and the vascular choroid. Normal eyes typically have maculas that are free of such deposits, although deposition can be abundant in the retinal periphery. The presence of soft deposits in the macula absent loss of macular vision per se is considered an early stage of age-related macular degeneration (AMD).

AMD is the major cause of severe visual loss in United States citizens over the age of 55. Most AMD patients have a buildup of deposits within and under the RPE in the macular region, which can result in atrophy of the retina and the RPE itself. Normally, retinal pigment cells are long-lived. They serve to scavenge photoreceptor discs from the rods and cones over the course of years, resulting in the accumulation of intracellular wastes. The incompletely digested residues reduce cytoplasmic space in the RPE cells, and can interfere with metabolism. As the cell volume available to the organelles diminishes, the capacity to digest photoreceptors decreases, which might be a factor in the onset and worsening of macular degeneration.

AMD occurs in either an atrophic or an exudative form. In exudative AMD, blood vessels grow from the choriocapillaris through defects in Bruch's membrane and, in some cases, the underlying RPE. Organization of serous or hemorrhagic exudates escaping from these vessels can result in fibrous scarring of the macular region with attendant degeneration of the neuroretina and permanent loss of central vision.

Another important class of ocular condition results from undesirable neovascularization in the eye. Neovascularization is a serious complication of a large variety of ocular disorders affecting the various tissues of the eye because it can lead to blindness. Corneal neovascularization occurs in many conditions and diseases, including trauma, chemical burns, and corneal transplantation.

Corneal transplantation is successful in many patients because of the absence of blood vessels in the corneal tissue. Because there are no blood vessels in the cornea, the circulating components of the immune system are not exposed to the new cornea and there is normally no problem of host-graft rejection. Induction of neovascularization in the cornea would expose the cornea to the immune system and lead to graft rejection. In addition, a subsequent graft is less likely to be successful. Treatments of these various causes of neovascularization can include the administration of immunosuppressives to modulate the inflammatory process, including neovascularization. However, immunosuppressives can inhibit appropriate wound healing in the cornea and can interfere with the ability to fight infections. Delayed wound healing leaves the cornea vulnerable to infections for longer periods. Hence, vision-threatening infections can result from current treatments.

Choroidal neovascularization (CNV) occurs incident to many ocular disorders, and is often associated with the proliferation of choroidal endothelial cells, overproduction of extracellular matrix, and formation of a fibrovascular subretinal membrane. RPE cell proliferation and production of angiogenic factors also appears to affect CNV. Choroidal neovascularization is caused by such retinal disorders as age-related macular degeneration, presumed ocular histoplasmosis syndrome, myopic degeneration, angioid streaks and ocular trauma. Macular degeneration was discussed above. Choroidal neovascularization has proven recalcitrant to treatment in most cases. In only 10% of cases can laser photocoagulation be attempted. There is no other treatment available. Even with successful laser photocoagulation, neovascularization recurs in about 60-70% of eyes.

Neovascularization of the iris, and its attendant scarring can result in glaucoma and blindness. Neovascularization of this portion of the eye can arise as a consequence of diabetic retinopathy, venous occlusion, ocular tumors and retinal detachment. Most commonly, laser treatment to cauterize the blood vessels is tried; however, that has the attendant risk of causing additional scarring.

Retinal and intravitreal neovascularization occurs in a wide range of disorders including diabetic retinopathy, vein occlusions, sickle cell retinopathy, retinopathy of prematurity, retinal detachment, ocular ischemia, and trauma.

Subretinal pigment epithelial and sub-retinal neovascularization are common, yet very severe, disorders of the eye. The growth of new blood vessels interferes with the normal anatomy of the visual and pigmentary cells in the eye, leading to severe visual loss. The new blood vessels leak fluid and blood under the macula causing marked distortion and loss of vision. When these blood vessels develop in the avascular foveal region of the eye, the result is central visual loss and legal blindness.

Absent specific trauma, the specific causes of these types of neovascularization are unknown; however, this disease most often affects patients over the age of 50 years old, who may or may not have a family history of subfoveal neovascularization. The visual loss is usually sufficient to result in legal blindness. There is no proven treatment once the blood vessels invade the foveal region. In fact, there are few warning signs that a patient is developing this disorder and there are no preventative measures. Even under close monitoring by an ophthalmologist, patients with subfoveal neovascularization have a poor prognosis.

Diabetic retinopathy is an ocular disorder that develops secondary to diabetes. It is characterized by thickening of capillary basement membranes and a lack of contact between pericytes and endothelial cells of the capillaries. Loss of pericytes increases leakage of the capillaries, which can lead to a breakdown of the blood-retina barrier.

Proliferative vitreoretinopathy is associated with proliferation of cellular and fibrotic membranes within the vitreous membranes and on the surfaces of the retina. RPE cell proliferation and migration is frequently observed. The membranes associated with proliferative vitreoretinopathy often contain extracellular matrix components such as collagen types I, II, and IV, and fibronectin, and become progressively fibrotic.

Uveitis refers to inflammation of the uveal tract. It includes iritis, cyclitis, and iridocyclitis and choroiditis, and usually occurs with inflammation of additional structures of the eye. This disorder has a variety of causes but is typically treated with systemic steroids, topical steroids, or cyclosporin. The disease frequently presents with a chronic inflammation occurring either in the anterior segment (70%) or in the posterior segment (30%), which can be complicated by episodes of severe exacerbation that frequently is not controllable with conventional medications. Reports in the literature suggest that 30,000 individuals become legally blind each year in the United States from uveitis. In addition, an estimated 20,000 individuals suffer significant loss of visual acuity from this disorder.

Sjogren's syndrome is an immune system disorder which manifests itself in the eyes as conjunctival and corneal dryness (keratoconjunctivitis sicca syndrome), and typically presents as a gritty sensation in the eyes. A lack of tear production resulting from functional destruction of the lacrimal glands by progressive mononuclear cell infiltrate and scarring of the gland. If the cornea is too dry, corneal ulcerations can develop. Current treatments are limited to symptomatic relief of ocular dryness.

The cornea and conjunctiva are also vulnerable to damage from pathogenic agents or direct trauma, drying associated with disorders of tearing, exposure to radiant energy (ultraviolet light, sun and welding guns), allergens such as pollen and mold, and infectious agents. Keratoconjunctivitis can also occur in patients with Stevens-Johnson syndrome, Wegener's granulomatosis, rheumatoid arthritis, atopic dermatitis and cicatricial pemphigoid. Corneal ulcers may occur. Wound healing disorders can also lead to severe ocular tissue damage via activation of inflammatory cells, release of growth factors and cytokines, proliferation and differentiation of ocular cells, increased capillary permeability, alterations in basement membrane matrix composition, increased deposition of extracellular matrix, fibrosis, neovascularization, and tissue remodeling.

For example, after corneal surgery, the cornea must heal. Popular types of corneal surgery include cataract extraction with or without lens replacement; corneal transplants to treat viral infection or penetrating keratoplasty (PKP); glaucoma filtration surgery; and radial keratotomy and other types of surgery to correct refraction. Cataract incisions are typically full thickness wounds in the cornea that can be as large as 8 mm in length with conventional intraocular lenses (IOLs) and as small as 3 mm or less with foldable silicone IOLs. These wounds generally heal without difficulty, although they take several months to stabilize and are associated with warpage of the corneal tissues leading to permanent astigmatism.

Penetrating keratoplasty (PKP) and corneal transplants are also characterized by full-thickness wounds around the entire circumference of the cornea. These wounds tend to remain weak for one or more years. Patients experience drift in visual acuity and increasing risk of wound dehiscence and/or endophthalmitis.

Radial keratotomy (RK) is the most widespread technique for altering the shape of the cornea. A commonly used form of RK places 4-8 surgical incisions in a radial pattern across the cornea. These incisions are typically 70-80% of the depth of the cornea, and are therefore non-penetrating wounds.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides methods for modulating eye damage associated with a disease or disorder, and/or damage incident to trauma including but not limited to blunt trauma, penetrating trauma, and trauma associated with ocular surgery. In some embodiments, the methods comprise administering to a subject an effective amount of a modulator of a migration inhibitory factor (MIF) polypeptide biological activity. In some embodiments, the disease or disorder is selected from the group consisting of dry macular degeneration; wet macular degeneration; retinopathy of prematurity; background diabetic retinopathy; proliferative diabetic retinopathy; sickle cell retinopathy; other vascular retinopathies; intraocular scarring; proliferative vitreoretinopathy; autoimmune uveitis; autoimmune uveoretinitis; uveitis of various etiologies; dry eye syndrome with and without Sjogren's syndrome; blunt, penetrating, or perforating ocular trauma and related ocular pathologies; open angle glaucoma; and secondary glaucoma; as well as various structural disorders of the eye that require cell transplantation for tissue engineering. In some embodiments, the damage incident to ocular surgery comprises scar formation and/or the administering step modulates a wound healing response in the eye on which the surgery was performed. In some embodiments, the disease or disorder is dry macular degeneration or wet macular degeneration.

In some embodiments, the presently disclosed subject matter provides methods for modulating the severity of, delaying the onset of, and/or inhibiting and/or preventing the development of an ocular disease. In some embodiments, the methods comprise contacting a migration inhibitory factor (MIF) polypeptide present within the eye of a subject with an effective amount of a modulator of a migration inhibitory factor (MIF) polypeptide biological activity, wherein a biological activity of the migration inhibitory factor (MIF) polypeptide in the eye of the subject is modulated, thereby reducing the severity of, delaying the onset of, and/or inhibiting and/or preventing the development of an ocular disease in the subject.

In some embodiments, the presently disclosed subject matter provides methods for modulating the severity of, delaying the onset of, and/or inhibiting and/or preventing the development of scarring and/or other consequence of wound healing incident to trauma including, but not limited to trauma associated with ocular surgery. In some embodiments, the methods comprise contacting a migration inhibitory factor (MIF) polypeptide present within the eye of a subject with an effective amount of a modulator of a migration inhibitory factor (MIF) polypeptide biological activity, wherein a biological activity of the migration inhibitory factor (MIF) polypeptide in the eye of the subject is modulated, thereby reducing the severity of, delaying the onset of, and/or inhibiting and/or preventing the development of scarring and/or other consequence of wound healing in the subject.

In some embodiments of the presently disclosed subject matter, the methods further comprise administering a second therapeutic agent selected from the group consisting of a modulator of angiogenesis, a modulator of fibrosis, and a modulator of inflammation. In some embodiments, the modulator of angiogenesis comprises a modulator of a vascular endothelial growth factor (VEGF) polypeptide biological activity. In some embodiments, the VEGF modulator comprises an antibody, optionally a monoclonal antibody, and further optionally a humanized monoclonal antibody, or a fragment or derivative thereof that comprises an $F_{ab}$ domain that binds to a VEGF polypeptide and/or a VEGF receptor polypeptide to thereby modulate VEGF-induced signal transduction in a cell of the eye. In some embodiments, the VEGF modulator is selected from the group consisting of ranibizumab and bevacizumab. In some embodiments, the modulator of fibrosis and/or the modulator of inflammation is selected from the group consisting of mitomycin, a corticosteroid, an immunosuppressive or cytotoxic, an anti-inflammatory biologic and/or a non-steroidal anti-inflammatory drug.

In some embodiments, the presently disclosed subject matter provides methods for modulating proliferation of a retinal pigment epithelial (RPE) cell. In some embodiments, the methods comprise contacting a migration inhibitory factor (MIF) polypeptide present in the RPE cell with an effective amount of a modulator of the MIF polypeptide, whereby proliferation of the RPE cell is modulated.

In some embodiments, the presently disclosed subject matter provides methods for inhibiting choroidal neovascularization (CNV), proliferative vitreoretinopathy (PVR), epithelio-mesenchymal transformation (EMT; optionally ocular EMT), or combinations thereof in a subject. In some embodiments, the methods comprise contacting a migration inhibitory factor (MIF) polypeptide present in the subject with an effective amount of a modulator of a MIF biological activity, whereby CNV, PVR, EMT, or combinations thereof are inhibited.

In some embodiments, the modulator of the migration inhibitory factor (MIF) polypeptide biological activity is an inhibitor or antagonist of a migration inhibitory factor (MIF) polypeptide biological activity. In some embodiments of the presently disclosed subject matter, the modulator of a migration inhibitory factor (MIF) polypeptide biological activity has the following structure:

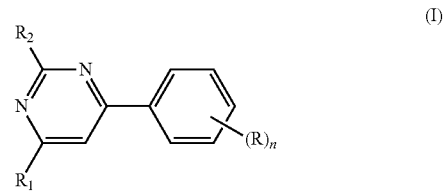

wherein:
each R is independently H, halo, OH, alkyl, substituted alkyl, aryl, amino, or carboxyl;
$R_1$ is H, halo, OH, alkyl, substituted alkyl, or aryl;
$R_2$ is H, halo, OH, alkyl, substituted alkyl, aryl, or amino; and
n is an integer from 0 to 5.

In some embodiments of Formula (I), $R_1$ is iodo, and optionally, $R_2$ is H and n is 0.

In some embodiments, the modulator the migration inhibitory factor (MIF) polypeptide biological activity is 4-iodo-6-phenylpyrimidine, 4-(2-fluorophenyl)-6-iodopyrimidine, or an analog or derivative thereof. In some embodiments, the modulator of the migration inhibitory factor (MIF) polypeptide biological activity has one of the following structures:

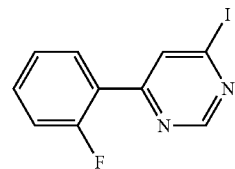

4-(2-fluorophenyl)-6-iodopyrimidine (Compound 1)

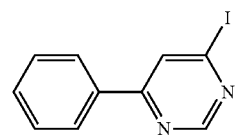 [SMILES: Ic1cc(-c2ccccc2)ncn1]

4-iodo-6-phenylpyrimidine (4-IPP; Compound 2)

In some embodiments, the analog or derivative of 4-iodo-6-phenylpyrimidine, 4-(2-fluorophenyl)-6-iodopyrimidine is selected from the group consisting of 4-iodo-6-phenylpyrimidine; 4-(2-fluorophenyl)-6-iodopyrimidine; 4-Iodo-6-(2,3-difluoro-4-methoxyphenyl)pyrimidine; 4-Iodo-6-(2-fluoro-4-methoxyphenyl)pyrimidine; 4-Iodo-6-(2-fluorophenyl)pyrimidine; 4-Iodo-6-(4-fluorophenyl) pyrimidine; 4-Iodo-6-(furan-3-yl)pyrimidine; 4-Iodo-6-(pyridin-3-yl)pyrimidine; 4-Iodo-6-(3-fluorophenyl) pyrimidine; 4-Iodo-6-(4-tert-butyloxymethylphenyl) pyrimidine; 4-Iodo-6-(2-fluoropyridin-3-yl)pyrimidine; 4-Iodo-6-(furan-2-yl)pyrimidine; 4-Iodo-6-(4-fluoropyrimidin-3-yl)pyrimidine; 4-Iodo-6-(3-fluoro-4-methoxyphenyl) pyrimidine; 4-iodo-6-(2-chloropyridin-5-yl)pyrimidine; 4-iodo-6-(2-hydroxyphenyl)pyrimidine; 4-iodo-6-(2,4-difluorophenyl)pyrimidine; 4-iodo-6-(2-fluoro-6-methoxyphenyl)pyrimidine; 4-iodo-6-(2-chlorophenyl)pyrimidine; 4-iodo-6-(3-acetylaminophenyl)pyrimidine; 4-iodo-6-(thiophen-3-yl)pyrimidine; 4-iodo-6-(3-hydroxymethylphenyl)pyrimidine; 4-iodo-6-(isoquinolin-4-yl)pyrimidine; 4-iodo-6-(2,4,5-trifluorophenyl)pyrimidine; 4-iodo-6-(2,4-difluoropyridin-3-yl)pyrimidine; 4-iodo-6-(4-methoxypyridin-3-yl)pyrimidine; 4-iodo-6-(thiophen-2-yl)pyrimidine; 4-iodo-6-(3,4-difluorophenyl)pyrimidine; 4-iodo-6-(4-ethoxyphenyl)pyrimidine; 4-iodo-6-(4-aminocarbonylphenyl)pyrimidine; 4-iodo-6-(3-aminocarbonylphenyl)pyrimidine; 4-iodo-6-(quinolin-4-yl)pyrimidine; 4-iodo-6-(quinolin-8yl)pyrimidine; 4-iodo-6-(quinolin-3-yl) pyrimidine; 4-iodo-6-(isoquinolin-5-yl)pyrimidine; 2-Methylthio-4-iodo-6-phenylpyrimidine; 2-Ethylthio-4-iodo-6-phenylpyrimidine; 2-Isopropylthio-4-iodo-6-phenylpyrimidine; 2-n-Butylthio-4-iodo-6-phenylpyrimidine; 2-Methylamino-4-iodo-6-phenylpyrimidine; 2-Ethylamino-4-iodo-6-phenylpyrimidine; 2-Propylamino-4-iodo-6-phenylpyrimidine; 2-Isopropylamino-4-iodo-6-phenylpyrimidine; 2-n-Butylamino-4-iodo-6-phenylpyrimidine; 4-iodo-6-(benzothiophen-2-yl)pyrimidine; 4-iodo-6-(benzofuran-2-yl)pyrimidine; 4-iodo-6-(4-hydroxybenzothiophen-2-yl) pyrimidine; 4-iodo-6-(4-acetylaminobenzothiophen-2-yl) pyrimidine; 4-iodo-6-(4-aminocarbonylbenzothiophen-2-yl) pyrimidine; 4-iodo-6-(5-acetylaminopyridin-3-yl) pyrimidine; 4-iodo-6-(5-aminocarbonylpyridin-3-yl) pyrimidine; 4-iodo-6-(4-fluoropyridin-3-yl)pyrimidine; 4-iodo-6-(4-acetylaminothiophen-2-yl)pyrimidine; 4-iodo-6-(4-aminocarbonylthiophen-2-yl)pyrimidine; and 4-iodo-6-(4-methoxythiophen-2-yl)pyrimidine.

In some embodiments of the presently disclosed subject matter, the modulator of a migration inhibitory factor (MIF) polypeptide biological activity comprises or encodes a nucleotide sequence that downregulates expression of a MIF gene product by RNA interference.

In some embodiments of the presently disclosed subject matter, the modulator of a migration inhibitory factor (MIF) polypeptide biological activity comprises an anti-MIF antibody, or a fragment or derivative thereof. In some embodiments, the anti-MIF antibody, or the fragment or derivative thereof comprises at least one antigen binding site (e.g., the paratope).

In some embodiments of the presently disclosed subject matter, the MIF polypeptide is a mammalian MIF polypeptide. In some embodiments, the MIF polypeptide is a human MIF polypeptide, optionally comprising the amino acid sequence disclosed in GENBANK® Accession No. NP_002406 and/or is encoded by a human MIF genetic locus present on chromosome 22. In some embodiments, the modulator of the migration inhibitory factor (MIF) polypeptide biological activity forms a stable covalent and/or non-covalent interaction with one or more of Pro-1, Met-2, Lys-32, Pro-33, Tyr-36, His-62, Ser-63, Ile-64, Lys-66, Tyr-95, Met-101, Val-106, Trp-108, and Phe-113 of a human MIF polypeptide, or forms a stable covalent and/or non-covalent interaction with one or more amino acids that correspond to any of these amino acids in a non-human MIF polypeptide.

In some embodiments of the presently disclosed subject matter, the modulator of the migration inhibitory factor (MIF) polypeptide biological activity is provided in a pharmaceutically acceptable composition. In some embodiments, the pharmaceutically acceptable composition is acceptable for use in a human. In some embodiments, the modulator of the migration inhibitory factor (MIF) polypeptide biological activity is provided in a form acceptable for systemic administration, optionally systemic administration by intravenous administration or oral administration. In some embodiments, the modulator of the migration inhibitory factor (MIF) polypeptide biological activity is provided in a form acceptable for direct or indirect administration to the eye, optionally for application to an external surface of the eye.

In some embodiments of the presently disclosed subject matter, the pharmaceutically acceptable composition comprises a liposome and/or a nanoparticle in which the modulator of the migration inhibitory factor (MIF) polypeptide biological activity is encapsulated and/or attached. In some embodiments, the liposome and/or the nanoparticle comprises a targeting ligand that targets the liposome and/or the nanoparticle to the eye or a structure within the eye. In some embodiments, the nanoparticle is constructed from one or more biocompatible polymers. In some embodiments, the nanoparticle is constructed from one or more biodegradable polymers. In some embodiments, the at least one of the one or more biodegradable polymers is selected from the group consisting of poly(lactic acid) (PLA), poly(glycolic acid) (PGA), polycaprolactone (PCL), a copolymer of lactic acid and glycolic acid (PLGA), a copolymer of lactic acid and caprolactone, polyepsilon caprolactone, polyhyroxy butyric acid, a poly(ortho)ester, a polyurethane, a polyanhydride, a polyacetal, a polydihydropyran, and a polycyanoacrylate. In some embodiments, the nanoparticle has a diameter from about 10 nm to about 500 nm.

In some embodiments, the modulator of the migration inhibitory factor (MIF) polypeptide biological activity is provided in a vehicle comprising a multifunctional microcyclic carrier. In some embodiments, the vehicle comprises a cyclic 1,4,7,10-tetraazacyclododecane-1,4,7,10-tetraacetic acid (DOTA) scaffold to which two cell-penetrating TAT peptides (L22) and a fluorescein isothiocyanate (FITC) molecule has been attached.

In some embodiments of the presently disclosed subject matter, the modulator of the migration inhibitory factor (MIF) polypeptide biological activity is an enhancer or an agonist of the migration inhibitory factor (MIF) polypeptide biological activity. In some embodiments, the enhancer or the agonist of the migration inhibitory factor (MIF) polypeptide biological activity enhances dimerization of a MIF receptor to which a MIF polypeptide binds.

The presently disclosed subject matter also provides methods for protecting photoreceptor cells in a subject with a detached retina. In some embodiments, the methods comprise contacting a migration inhibitory factor (MIF) polypeptide present within the eye of a subject with a modulator of a migration inhibitory factor (MIF) polypeptide biological activity as defined herein, wherein a biological activity of the migration inhibitory factor (MIF) polypeptide in the eye of the subject is modulated, thereby protecting photoreceptor cells in the detached retina of a subject in the subject. In some embodiments, the modulator has the following structure:

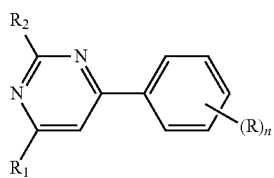

(I)

wherein each R is independently H, halo, OH, alkyl, substituted alkyl, aryl, amino, or carboxyl; $R_1$ is H, halo, OH, alkyl, substituted alkyl, or aryl; $R_2$ is H, halo, OH, alkyl, substituted alkyl, aryl, or amino; and n is an integer from 0 to 5. In some embodiments, $R_1$ is iodo, and optionally, $R_2$ is H and n is 0. In some embodiments, the modulator is 4-iodo-6-phenylpyrimidine, 4-(2-fluorophenyl)-6-iodopyrimidine, or an analog or derivative thereof.

It is thus an object of the presently disclosed subject matter to provide methods for modulating eye damage associated with a disease, condition, disorder, or trauma.

An object of the presently disclosed subject matter having been stated herein above, and which is achieved in whole or in part by the presently disclosed subject matter, other objects will become evident as the description proceeds when taken in connection with the accompanying drawings as best described herein below.

BRIEF DESCRIPTION OF THE FIGURES

FIGS. 5A-5E are photomicrographs of the eyes of vehicle-only control mice mouse showing the development of pre-retinal (arrows in FIG. 5A) and subretinal (arrows in FIG. 5B) membranes indicative of PVR; and also that RPE cells built up multiple layers in the subretinal space (area between the arrows in FIG. 5C and shown by the arrow in FIG. 5D), a feature associated with EMT, and also that epiretinal membranes formed by fusiform RPE cells (arrow in FIG. 5E) sometimes bridged the opposing retinal segments.

FIGS. 5F and 5G are a series of photomicrographs of the eyes of animals that were treated with the small molecule MIF inhibitor Compound 1.

FIGS. 5H and 5I are a series of photomicrographs of the eyes of a second model of PVR in Brown Norway rats. In FIG. 5H, RPE cells of the animals treated with the small molecule MIF inhibitor Compound 1 maintained their epitheloid morphology and did not invade the subretinal and/or intravitreal space. However, RPE cells in control animals that received phosphate-buffered saline became migratory in the vitreous and started to form epiretinal membranes (arrows in FIG. 5I).

FIG. 6A shows that photoreceptor cells in the detached retina (between the arrows) were better preserved compared with the control rat that received the vehicle.

FIG. 9A is a photomicrograph of the eye of a control animal (vehicle alone), and FIG. 9B is a photomicrograph of the eye of an animal treated with the small molecule MIF inhibitor Compound 1. Comparing FIGS. 9A and 9B confirmed better resurfacing of the denuded Bruch's membrane with RPE cells in animals treated with Compound 1 (arrows in FIG. 9B) compared with control animals (FIG. 9A).

In FIG. 10A, comparison of the PCNA staining in the MIF neutralized animals to that in the vehicle control animals demonstrated that MIF neutralization resulted in higher proliferation of the RPE cells, which contributed to better surface coverage in the $NalO_3$ model of geographic atrophy. Similarly, the TUNEL staining depicted in FIG. 10B also demonstrated that MIF neutralized animals showed decreased apoptotic cell death as compared to vehicle control mice.

FIGS. 11A and 11B depict histological analyses of vehicle control mice, and show that in these animals, choroidal new vessels gained access to the subretinal space through the breaks of the Bruch's membrane and RPE monolayer (arrows in FIGS. 11A and 11B). In FIG. 11C, retinal pigment epithelium (RPE) was observed to proliferate over the laser spot and seal it off from neovascularization (arrows in FIG. 11C), blocking the ingrowth of choroidal new vessels.

BRIEF DESCRIPTION OF THE SEQUENCE LISTING

Figure 1:
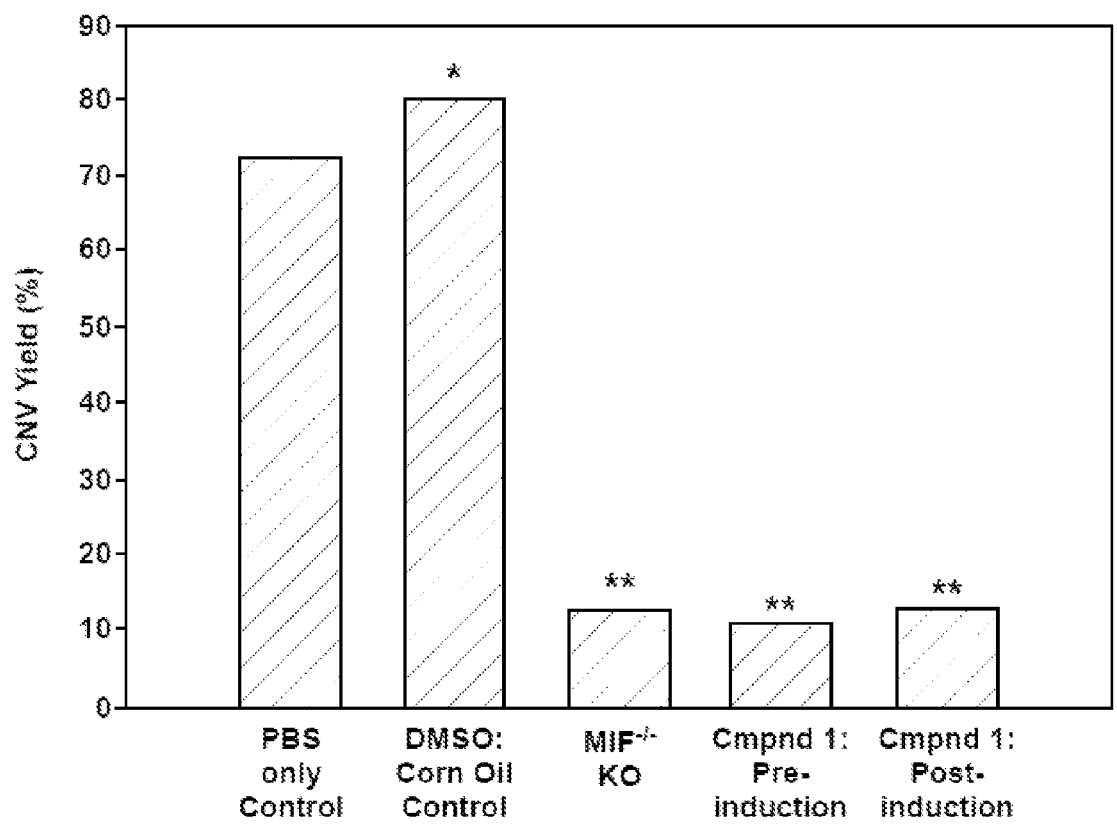
FIG. 1 is a bar graph showing the effect of an exemplary MIF modulator 4-(2-fluorophenyl)-6-iodopyrimidine (Compound 1) on subretinal choroidal neovascularization. The left-most bar (i.e., Bar 1) is a phosphate-buffered saline (PBS) only control. Bar 2 is a vehicle (dimethylsulfoxide (DMSO): corn oil) control. Bar 3 is the result in $MIF^{-/-}$ knockout (KO) mice. Bar 4 is Compound 1 before twenty-four (24) hours prior to induction of neovascularization with a laser. Bar 5 is Compound 1 ten (10) days after induction of neovascularization with a laser. *: p=0.5; **: p=0.0001.

SEQ ID NOs: 1 and 2 are nucleotide and amino acid sequences disclosed in Accession Nos. NM_002415 and NP_002406, respectively, of the GENBANK® database. SEQ ID NO: 1 corresponds to the nucleotide sequence of a 561 basepair *Homo sapiens* macrophage migration inhibitory factor (glycosylation-inhibiting factor; MIF) gene product. Nucleotides 98-445 of SEQ ID NO: 1 includes an open reading frame that encodes a MIF polypeptide, the amino acid sequence of which is present in the GENBANK® database as Accession No. NP_002406 and that is disclosed as SEQ ID NO: 2. The GENBANK® Accession Nos. NM_002415 and NP_002406, including all annotations present therein, are incorporated by reference in their entireties.

DETAILED DESCRIPTION

I. General Considerations

Macrophage Migration Inhibitory Factor (MIF) is one of the earliest described cytokines, and is an immunoregulatory protein with a wide variety of biological activities (see e.g., Swope et al., 1999; Metz et al., 1997; Bucala, 1996). Originally, MIF was found to be secreted by activated lymphoid cells, to inhibit the random migration of macrophages, and to be associated with delayed-type hypersensitivity reactions (George et al., 1962; Weiser et al., 1981; Bloom et al., 1966; David, 1966). MIF was also shown to enhance macrophage adherence, phagocytosis, and tumoricidal activity (Nathan et al., 1971; Nathan et al., 1973; Churchill et al., 1975). Unfortunately, many of the early MIF studies used mixed-culture supernatants that were shown later to contain other cytokines, such as IFN-γ and IL-4, which also have macrophage migration inhibitory activity (Thurman et al., 1985; McInnes et al., 1988). The availability of recombinant MIF has allowed for confirmation of these biological activities, and for the identification of additional activities.

Recombinant human MIF was originally cloned from a human T cell library (Weiser et al., 1989), and was shown to activate blood-derived macrophages to kill intracellular parasites and tumor cells in vitro, to stimulate IL-1β and TNF-α expression, and to induce nitric oxide synthesis (Weiser et al., 1991; Pozzi et al., 1992; Weiser et al., 1992; Cunha et al., 1993). While the conclusions available from several of these early reports are confounded by the presence of a bioactive mitogenic contaminant in the recombinant MIF preparations used, the potent pro-inflammatory activities of MIF have been established in other studies that do not suffer from this complicating factor (reviewed in Bucala, 1996).

More recent MIF studies have capitalized on the production of recombinant MIF in purified form as well as the development of MIF-specific polyclonal and monoclonal antibodies to establish the biological role of MIF in a variety of normal homeostatic and pathophysiological settings (reviewed in Rice et al., 1998). Among the most important insights of these later reports has been the recognition that MIF not only is a cytokine product of the immune system, but also is a hormone-like product of the endocrine system, particularly the pituitary gland. This work has underscored the potent activity of MIF as a counter-regulator of the anti-inflammatory effects of the glucocorticoids (both those endogenously released and those therapeutically administered), with the effect that the normal activities of glucocorticoids to limit and suppress the severity of inflammatory responses are inhibited by MIF. The endogenous MIF response is thus seen as a cause or an exacerbative factor in a variety of inflammatory diseases and conditions (reviewed in Donnelly et al., 1997).

MIF is now known to have several biological functions beyond its well-known association with delayed-type hypersensitivity reactions. For example, as mentioned above, MIF released by macrophages and T cells acts as a pituitary mediator in response to physiological concentrations of glucocorticoids (Bucala, 1996). This leads to an overriding effect of glucocorticoid immunosuppressive activity through alterations in TNF-α IL-1β, IL-6, and IL-8 levels. Additional biological activities of MIF include the regulation of stimulated T cells (Bacher et al., 1996), the control of IgE synthesis (Mikayama et al., 1993), the functional inactivation of the p53 tumor suppressor protein (Hudson et al., 1999), the regulation of glucose and carbohydrate metabolism (Sakaue et al., 1999), and the attenuation of tumor cell growth and tumor angiogenesis (Chesney et al., 1999; Shimizu et al., 1999).

II. DEFINITIONS

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the Statements of the Presently Disclosed Subject Matter. Thus, for example, reference to "a cell" includes a plurality of such cells, and so forth.

Unless otherwise indicated, all numbers expressing quantities of ingredients, reaction conditions, and so forth used in the specification and Statements of the Presently Disclosed Subject Matter are to be understood as being modified in all instances by the term "about". Accordingly, unless indicated to the contrary, the numerical parameters set forth in this specification and attached Statements of the Presently Disclosed Subject Matter are approximations that can vary depending upon the desired properties sought to be obtained by the presently disclosed subject matter.

The term "about", as used herein when referring to a measurable value such as an amount of weight, time, dose, etc., is meant to encompass variations of in some embodiments ±20%, in some embodiments ±10%, in some embodiments ±5%, in some embodiments ±1%, and in some embodiments ±0.1% from the specified amount, as such variations are appropriate to perform the disclosed methods.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. For example, when the phrase "consists of" appears in a clause of the body of a Statement of the Presently Disclosed Subject Matter, rather than immediately following the preamble, it limits only the element set forth in that clause; other elements are not excluded from the Statement of the Presently Disclosed Subject Matter as a whole.

As used herein, the phrase "consisting essentially of" limits the scope of the related disclosure or Statement of the Presently Disclosed Subject Matter to the specified materials and/or steps, plus those that do not materially affect the basic and novel characteristic(s) of the disclosed subject matter. For example, a pharmaceutical and/or therapeutic composition of the presently disclosed subject matter can "consist essentially of" an active agent (e.g., a modulator or a MIF biological activity), which means that the recited active agent is the only active agent present in the pharmaceutical and/or therapeutic composition that is designed to modulate a MIF biological activity. It is noted, however, that additional components that are present in the pharmaceutical and/or therapeutic composition can include carriers, excipients, buffers, salts, etc.

With respect to the terms "comprising", "consisting essentially of", and "consisting of", where one of these three terms is used herein, the presently disclosed subject matter can include the use of either of the other two terms. For example, the presently disclosed subject matter relates in some embodiments to methods for modulating or preventing eye damage associated with a disease or disorder, and/or damage incident to ocular surgery, the method comprising administering to a subject an effective amount of a modulator of a MIF polypeptide biological activity. It is understood that the presently disclosed subject matter thus also encompasses methods that in some embodiments consist essentially of administering to a subject an effective amount of a modulator of a MIF polypeptide biological activity, as well as methods that in some embodiments consist of administering to a subject an effective amount of a modulator of a MIF polypeptide biological activity. As such, it is understood that in some embodiments the methods of the presently disclosed subject matter comprise the step(s) that is/are disclosed herein, in some embodiments the methods of the presently disclosed subject matter consist essentially of the step(s) that is/are disclosed herein, and in some embodiments the methods of the presently disclosed subject matter consist of the step(s) that is/are disclosed herein.

The term "biological activity" as used herein with reference to a particular biologically-active molecule, such as a polypeptide (e.g., MIF) is inclusive of any biological or enzymatic activity by the molecule on another molecule or substrate. For example, with reference to MIF, "biological activity" includes but is not limited to inhibition of Th1 lymphocyte responses (Abe et al., 2001), transcription regulation (e.g., of cyclin D1 expression; Liao et al., 2003; Swant et al., 2005), cell migration promotion, cell invasion promotion, anchorage-independent growth promotion, angiogenesis promotion (Chesney et al., 1999; Shimizu et al., 1999; Ogawa et al., 2000; White et al., 2001; White et al., 2003), promotion of HIF-1α expression (Winner et al., 2007), arachidonic acid metabolism (Mitchell et al., 1999), E2F transcription factor regulation (Petrenko & Moll, 2005), Rb inactivation (Liao et al., 2003; Swant et al., 2005), and p53 inhibition (Hudson et al., 1999; Mitchell et al., 2002). With reference to MIF, "biological activity" is also inclusive of enzymatic activities, such as, for example, tautomerase activity.

As used herein, the phrase "choroidal neovascularization" (CNV) refers to the creation of new blood vessels in the choroid layer of the eye. In some embodiments, CNV refers to the undesirable creation of new blood vessels in the choroid layer of the eye resulting from a disease, disorder, and/or trauma and their subsequent growth and invasion of the sub-RPE and.or subretinal space.

As used herein, the term "effective amount" means a dosage sufficient to provide treatment for the condition or disease state being treated. This can vary depending on the subject, the disease, and the treatment being effected.

As used herein, the phrase "epithelio-mesenchymal transformation" (EMT; sometimes referred to as "epithelial-mesenchymal transition") refers to a process by which the adhesion of epithelial cells is lost, leading to an increase in the ability of the cells to migrate (e.g., to migrate to different sites in an animal). EMT of the cells changes their phenotypical and behavioral characteristics and can lead to tissue destruction, distortion, scar formation, and/or loss of anatomical and functional properties of the associated tissues. In some embodiments, cells of the retinal pigment epithelium (RPE) can undergo EMT as a result of a disease or disorder and/or subsequent to ocular trauma, which can lead to undesirable proliferation and migration of the RPE.

The term "inflammatory disorder", as used herein refers to disorders involving the immune system, including disorders characterized by inflammation or participation of immune cells as a part of the pathobiology. Exemplary inflammatory disorders include but are not limited to autoimmune disorders and disorders associated with undesirable angiogenesis, such as age-related macular degeneration. "Inflammatory disorder", as the term is used herein is inclusive of autoimmune disorders. Exemplary autoimmune disorders include but are not limited to autoimmune uveitis and autoimmune uveoretinitis.

As such, the terms "inhibitor" and "antagonist" refers to a chemical substance that inhibits, that is inactivates or decreases, the biological activity of a polypeptide such as for example a MIF polypeptide.

As used herein, the term "modulate" means an increase, decrease, or other alteration of any, or all, biological activities or properties of a MIF polypeptide. The term "modulation" as used herein refers to both upregulation (i.e., activation or stimulation) and downregulation (i.e., inhibition or suppression) of a MIF biological activity. The term "modulate" as used herein can also refer to a change in the expression level of a gene, or a level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit" or "suppress", but the use of the word "modulate" is not limited to this definition.

The terms "operably linked" and "operatively linked" refer to two nucleic acid sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

The term "polynucleotide" refers to a polymer of two or more nucleic acids. The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., 1991; Ohtsuka et al., 1985; Rossolini et al., 1994). The terms "nucleic acid" or "nucleic acid sequence" can also be used interchangeably with gene, open reading frame (ORF), cDNA, and mRNA encoded by a gene.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

As used herein, the phrase "proliferative vitreoretinopathy" (PVR) refers to a complication of rhegmatogenous retinal detachment characterized by undesirable proliferation and migration of retinal pigmented epithelium (RPE). The REP can undergo epithelial-mesenchymal transition (EMT), resulting in the deposition of extracellular matrix in the vicinity of the detachment and the formation of fibrotic membranes in the retinal and subretinal space. PVR is classified into four Grades (A, B, C, and D) depending on the extent to which the RPE cells have proliferated and migrated as well as the location of the resulting scar tissue and the related retinal detachment.

As used herein, the term "stable interaction" with reference to an interaction of one or more amino acid residues of MIF and a compound disclosed herein refers to covalent and/or non-covalent interactions between the moieties, including but not limited to Van der Waals interactions, electrostatic forces, hydrogen bonding, or combinations thereof. In particular, disclosed herein is the interaction of an inhibitory compound (e.g., 4-(2-fluorophenyl)-6-iodopyrimidine and any analogs and derivatives thereof) with a Pro-1 of mature MIF. "Pro-1" refers to the first amino acid residue, in this case a proline (the N-terminal methionine of all MIF species is cleaved to reveal an N-terminal proline: i.e., Pro-1), of a mature MIF polypeptide (e.g., human MIF; GENBANK® Accession No. NP_002406, herein incorporated by reference in its entirety) as counted from the N-terminus of the mature MIF polypeptide. Likewise, "Lys-32", "Pro-33", and "Tyr-36" refers to the thirty-second amino acid (a lysine), the thirty-third amino acid (a proline), and the thirty-sixth amino acid (a tyrosine), respectively, as counted from the N-terminus of the mature MIF polypeptide. The numbering system employed herein does not include the N-terminal methionine (e.g., Met-1), which is removed during the maturation of the MIF polypeptide, as amino acid number 1. GENBANK® Accession No. NP_002406 (i.e., SEQ ID NO: 2), on the other hand, does begin its numbering at Met-1 and has Pro-2, Lys-33, Pro-34, and Tyr-37.

III. Modulators of MIF Polypeptide Biological Activities

III.A. Small Molecules

The presently disclosed subject matter provides compounds (e.g., small molecules) that form stable interactions with MIF and can thereby inhibit biological activities of MIF. In some embodiments, the compounds can form stable interactions with at least a proline at the N-terminal residue (Pro-1) of the MIF polypeptide. In particular embodiments, the compounds form stable interactions with a Pro-1 of each monomer of the MIF trimer (please see Winner et al., 2008 for detailed information). In some embodiments, the compound further forms a stable interaction with one or more of Met-2, Lys-32, Pro-3, Tyr-36, His-62, Ser-63, Ile-64, Lys-66, Tyr-95, Met-101, Val-106, Trp-108, and Phe-113 of the MIF polypeptide.

In some embodiments, the compound that stably interacts with MIF is 4-iodo-6-phenylpyrimidine or an analog, derivative, salt, solvate, or prodrug thereof. In some embodiments, the compound has a structure of Formula (I):

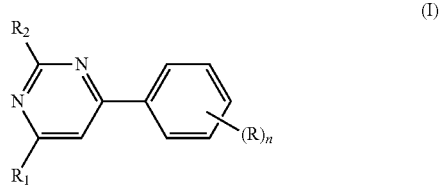

(I)

wherein:
each R is independently H, OH, alkyl, substituted alkyl, amino, or carboxyl;
$R_1$ is H, halo, OH, alkyl, or substituted alkyl;
$R_2$ is H, OH, alkyl, substituted alkyl, or amino; and
n is an integer from 0 to 5.

It is understood that any of the embodiments of R, $R_1$, $R_2$, and n of Formula (I) can be present with any of the other embodiments of R, $R_1$, $R_2$, and n of Formula (I), such that the structures that correspond to Formula (I) encompass all possible combinations and subcombinations of R, $R_1$, $R_2$, and n.

A named "R" (e.g., R, $R_1$, and $R_2$) group will generally have the structure that is recognized in the art as corresponding to a group having that name, unless specified otherwise herein. For the purposes of illustration, certain representative "R" groups as set forth herein are defined below. These definitions are intended to supplement and illustrate, not preclude, the definitions that would be apparent to one of ordinary skill in the art upon review of the present disclosure.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, aryl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl (forming a hydroxyalkyl, e.g., $(CH_2)_n$—OH, wherein n is 1-20), nitro, amino, alkylamino, dialkylamino, sulfate, and mercapto.

Further, as used herein, the terms alkyl and/or "substituted alkyl" include an "allyl" or an "allylic group." The terms "allylic group" or "allyl" refer to the group —$CH_2HC$=$CH_2$ and derivatives thereof formed by substitution. Thus, the terms alkyl and/or substituted alkyl include allyl groups, such as but not limited to, allyl, methylallyl, di-methylallyl, and the like. The term "allylic position" or "allylic site" refers to the saturated carbon atom of an allylic group. Thus, a group, such as a hydroxyl group or other substituent group, attached at an allylic site can be referred to as "allylic."

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A structure represented generally by a formula such as:

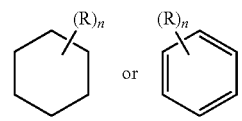

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. When n is 0, the structure is unsubstituted, and each atom on the ring is bonded to neighbor atoms on the ring and hydrogen atoms only. For example, when the structure is phenyl and n is zero, each carbon atom on the phenyl ring is bonded to one hydrogen only, although in keeping with structure drawing conventions in the art of organic chemistry, the hydrogen atoms are not shown. Each R group, if more than one, is substituted on an available carbon of the ring structure rather than on another R group. For example, the structure:

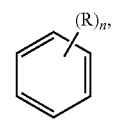

wherein n is an integer from 0 to 2 comprises compound groups including, but not limited to:

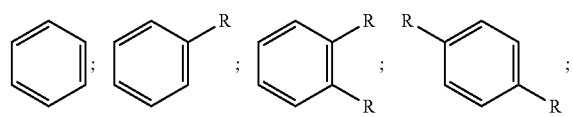

and the like (i.e., a 6-carbon aromatic ring with 0, 1, or 2 R groups, wherein for those with 2 R groups the individual R groups can be the same or different, and can be in ortho, meta, or para positions).

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

In some embodiments, the compounds described by the presently disclosed subject matter contain a linking group. As used herein, the term "linking group" comprises a chemical moiety, such as a furanyl, phenylene, thienyl, and pyrrolyl radical, which is bonded to two or more other chemical moieties, in particular aryl groups, to form a stable structure.

When a named atom of an aromatic ring or a heterocyclic aromatic ring is defined as being "absent," the named atom is replaced by a direct bond. When the linking group or spacer group is defined as being absent, the linking group or spacer group is replaced by a direct bond.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH═CH—CH═CH—; —CH═CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include, but are not limited to, cyclopropyl, cyclobutyl, cyclopentyl, cyclohexyl, cycloheptyl, and the like. Further, the cycloalkyl group can be optionally substituted with a linking group, such as an alkylene group as defined herein above, for example, methylene, ethylene, propylene, and the like. In such cases, the cycloalkyl group can be referred to as, for example, cyclopropylmethyl, cyclobutylmethyl, and the like. Additionally, multicyclic cycloalkyl rings include adamantyl, octahydronaphthyl, decalin, camphor, camphane, and noradamantyl.

"Alkoxyl" or "alkoxyalkyl" refer to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

"Aryloxyl" refers to an aryl-O— group wherein the aryl group is as previously described, including a substituted aryl.

The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

"Acylamino" refers to an acyl-NH— group wherein acyl is as previously described.

"Aroyl" refers to a R—CO— group, wherein R is an aromatic group that in some embodiments is derived from an aromatic carboxylic acid.

"Aroylamino" refers to an aroyl-NH— group wherein aroyl is as previously described.

The term "amino" refers to the —$NH_2$ group.

The term "carbonyl" refers to the —(C═O)— group.

The term "carboxyl" refers to the —COOH group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

When the phrase "independently selected" is used, the substituents being referred to (e.g., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, and the like.

In some embodiments, a modulator of MIF biological activity is 4-(2-fluorophenyl)-6-iodopyrimidine (Compound 1), which has the following structure:

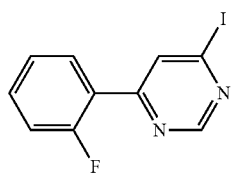 [SMILES: Fc1ccccc1-c1cc(I)ncn1]

In some embodiments, a modulator of MIF biological activity is 4-iodo-6-phenylpyrimidine (4-IPP; Compound 2), which has the following structure:

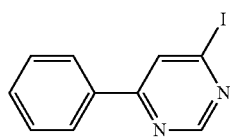

Additional small molecule modulators of MIF biological activities are disclosed in Cournia et al., 2009; McLean et al., 2009; Cho et al., 2010; Kithcart et al., 2010; Ouertatani-Sakouhi et al., 2010; Al-Abed & Van Patten, 2011; Hare et al., 2011; U.S. Pat. No. 6,492,428 to Al-Abed et al.; PCT International Patent Application Publication No. WO 2002/100332 of Al-Abed; PCT International Patent Application Publication No. WO 2005/034952 of Al-Abed; PCT International Patent Application Publication No. WO 2007/112015 of Al-Abed; PCT International Patent Application Publication No. WO 2007/112036 of Al-Abed; PCT International Patent Application Publication No. WO 2007/140263 of Mitchell et al. (the U.S. National Stage of which published as U.S. Patent Application Publication No. 2011/0009412); PCT International Patent Application Publication No. WO 2007/145888 of Al-Abed; PCT International Patent Application Publication No. WO 2009/085180 of Al-Abed; and PCT International Patent Application Publication No. WO 2011/038234 of Mitchell et al. The entirety of each of these publications is incorporated herein by reference.

By way of example and not limitation, small molecule modulators of MIF biological activities include the substituted iminoquinone or substituted orthoquinone compounds disclosed in U.S. Pat. No. 6,492,428 as Formulae I and II (including, but not limited to the compounds listed in Table I of U.S. Pat. No. 6,492,428); (S,R)-3-(4-hydroxyphenyl)-4,5-dihydro-5-isoxazole acetic acid methyl ester; N-benzyl-benzoxazol-2-one; 3-isobutyryl-2-isopropylpyrazolo-[1,5-a]pyridine; and derivatives thereof. Additional small molecule modulators of MIF biological activities include the compounds listed in Table 1 of PCT International Patent Application Publication No. 2011/038234, which include, but are not limited to 4-Iodo-6-(2,3-difluoro-4-methoxyphenyl)pyrimidine; 4-Iodo-6-(2-fluoro-4-methoxyphenyl)pyrimidine; 4-Iodo-6-(2-fluorophenyl)pyrimidine; 4-Iodo-6-(4-fluorophenyl)pyrimidine; 4-Iodo-6-(furan-3-yl)pyrimidine; 4-Iodo-6-(pyridin-3-yl)pyrimidine; 4-Iodo-6-(3-fluorophenyl)pyrimidine; 4-Iodo-6-(4-tert-butyloxymethylphenyl)pyrimidine; 4-Iodo-6-(2-fluoropyridin-3-yl)pyrimidine; 4-Iodo-6-(furan-2-yl)pyrimidine; 4-Iodo-6-(4-fluoropyrimidin-3-yl)pyrimidine; 4-Iodo-6-(3-fluoro-4-methoxyphenyl)pyrimidine; 4-iodo-6-(2-chloropyridin-5-yl)pyrimidine; 4-iodo-6-(2-hydroxyphenyl)pyrimidine; 4-iodo-6-(2,4-difluorophenyl)pyrimidine; 4-iodo-6-(2-fluoro-6-methoxyphenyl)pyrimidine; 4-iodo-6-(2-chlorophenyl)pyrimidine; 4-iodo-6-(3-acetylaminophenyl)pyrimidine; 4-iodo-6-(thiophen-3-yl)pyrimidine; 4-iodo-6-(3-hydroxymethylphenyl)pyrimidine; 4-iodo-6-(isoquinolin-4-yl)pyrimidine; 4-iodo-6-(2,4,5-trifluorophenyl)pyrimidine; 4-iodo-6-(2,4-difluoropyridin-3-yl)pyrimidine; 4-iodo-6-(4-methoxypyridin-3-yl)pyrimidine; 4-iodo-6-(thiophen-2-yl)pyrimidine; 4-iodo-6-(3,4-difluorophenyl)pyrimidine; 4-iodo-6-(4-ethoxyphenyl)pyrimidine; 4-iodo-6-(4-aminocarbonylphenyl)pyrimidine; 4-iodo-6-(3-aminocarbonylphenyl)pyrimidine; 4-iodo-6-(quinolin-4-yl)pyrimidine; 4-iodo-6-(quinolin-8yl)pyrimidine; 4-iodo-6-(quinolin-3-yl)pyrimidine; 4-iodo-6-(isoquinolin-5-yl)pyrimidine; 2-Methylthio-4-iodo-6-phenylpyrimidine; 2-Ethylthio-4-iodo-6-phenylpyrimidine; 2-Isopropylthio-4-iodo-6-phenylpyrimidine; 2-n-Butylthio-4-iodo-6-phenylpyrimidine; 2-Methylamino-4-iodo-6-phenylpyrimidine; 2-Ethylamino-4-iodo-6-phenylpyrimidine; 2-Propylamino-4-iodo-6-phenylpyrimidine; 2-Isopropylamino-4-iodo-6-phenylpyrimidine; 2-n-Butylamino-4-iodo-6-phenylpyrimidine; 4-iodo-6-(benzothiophen-2-yl)pyrimidine; 4-iodo-6-(benzofuran-2-yl)pyrimidine; 4-iodo-6-(4-hydroxybenzothiophen-2-yl)pyrimidine; 4-iodo-6-(4-acetylaminobenzothiophen-2-yl)pyrimidine; 4-iodo-6-(4-aminocarbonylbenzothiophen-2-yl)pyrimidine; 4-iodo-6-(5-acetylaminopyridin-3-yl)pyrimidine; 4-iodo-6-(5-aminocarbonylpyridin-3-yl)pyrimidine; 4-iodo-6-(4-fluoropyridin-3-yl)pyrimidine; 4-iodo-6-(4-acetylaminothiophen-2-yl)pyrimidine; 4-iodo-6-(4-aminocarbonylthiophen-2-yl)pyrimidine; and 4-iodo-6-(4-methoxythiophen-2-yl)pyrimidine.

As such, any of these small molecule modulators of MIF biological activities can be employed in the compositions and methods disclosed herein.

III.B. Nucleic Acid-Based Modulators

The presently disclosed subject matter provides nucleic acid-based modulators of MIF polypeptide biological activities. In some embodiments, the nucleic acid-based modulators comprise and/or encode antisense polynucleotides that have binding specificity for portions of a MIF coding sequence and can be used to modulate (e.g., inhibit) the expression of a MIF polynucleotide in a cell or tissue by contacting the cell or tissue with the antisense polynucleotide, thereby modulating a biological activity of a MIF polypeptide encoded thereby.

In some embodiments, the MIF polypeptide is a human MIF polypeptide. In some embodiments, the antisense polynucleotide comprises a nucleotide sequence having binding specificity for a subsequence of a human MIF gene product comprising a nucleotide sequence as set forth in GENBANK® Accession No. NM_002415 (i.e., SEQ ID NO: 1). In some embodiments, the antisense polynucleotide comprises a nucleotide sequence having binding specificity for a subsequence of a human MIF gene produce that is wholly or partially within nucleotides 98-445 of SEQ ID NO: 1, which corresponds to an open reading frame (ORF) of a human MIF gene product.

It is further provided that any subsequence of GENBANK® Accession No. NM_002415 can be selected as a target for RNAi based on the approaches disclosed herein (including, but not limited to any contiguous 19-25 nucleotide subsequence present in GENBANK® Accession No. NM_002415/SEQ ID NO: 1). Exemplary, non-limiting subsequences of GENBANK® Accession No. NM_002415/SEQ ID NO: 1 that can be targeted using antisense polynucleotides include, but are not limited to:

5'-GTTCATCGTAAACACCAAC-3' (SEQ ID NO: 3)
(i.e., nucleotides 106-124 of GENBANK®
Accession No. NM_002415;;

5'-CATCGTAAACACCAACGTG-3' (SEQ ID NO: 4)
(i.e., nucleotides 109-127 of GENBANK®
Accession No. NM_002415;;

5'-TCGTAAACACCAACGTGCC-3' (SEQ ID NO: 5)
(i.e., nucleotides 111-129 of GENBANK®
Accession No. NM_002415;;

5'-CGTAAACACCAACGTGCCC-3' (SEQ ID NO: 6)
(i.e., nucleotides 112-130 of GENBANK®
Accession No. NM_002415;;

5'-GGTTCCTCTCCGAGCTCAC-3' (SEQ ID NO: 7)
(i.e., nucleotides 150-168 of GENBANK®
Accession No. NM_002415;;

5'-ACATCGCGGTGCACGTGGT-3' (SEQ ID NO: 8)
(i.e., nucleotides 207-225 of GENBANK®
Accession No. NM_002415;;

5'-GGACCAGCTCATGGCCTTC-3' (SEQ ID NO: 9)
(i.e., nucleotides 229-247 of GENBANK®
Accession No. NM_002415;;

5'-GCCTGCACAGCATCGGCAA-3' (SEQ ID NO: 10)
(i.e., nucleotides 279-297 of GENBANK®
Accession No. NM_002415;;

5'-CCTGCACAGCATCGGCAAG-3' (SEQ ID NO: 11)
(i.e., nucleotides 280-298 of GENBANK®
Accession No. NM_002415;;

5'-CTGCACAGCATCGGCAAGA-3' (SEQ ID NO: 12)
(i.e., nucleotides 281-299 of GENBANK®
Accession No. NM_002415;;

5'-GCGCAGAACCGCTCCTACA-3' (SEQ ID NO: 13)
(i.e., nucleotides 306-326 of GENBANK®
Accession No. NM_002415;;

5'-CAGAACCGCTCCTACAGCA-3' (SEQ ID NO: 14)
(i.e., nucleotides 311-329 of GENBANK®
Accession No. NM_002415;;

5'-AGAACCGCTCCTACAGCAA-3' (SEQ ID NO: 15)
(i.e., nucleotides 312-330 of GENBANK®
Accession No. NM_002415;;

5'-TCTACATCAACTATTACGA-3' (SEQ ID NO: 16)
(i.e., nucleotides 381-399 of GENBANK®
Accession No. NM_002415;;

5'-CTACATCAACTATTACGAC-3' (SEQ ID NO: 17)
(i.e., nucleotides 382-400 of GENBANK®
Accession No. NM_002415;;

5'-TACATCAACTATTACGACA-3' (SEQ ID NO: 18)
(i.e., nucleotides 383-401 of GENBANK®
Accession No. NM_002415;;

5'-ACATCAACSEQ ID NO: 19)TATTACGACAT-3' (SEQ ID NO: 19)
(i.e., nucleotides 384-402 of GENBANK®
Accession No. NM_002415;;

5'-CATCAACTATTACGACATG-3' (SEQ ID NO: 20)
(i.e., nucleotides 385-403 of GENBANK®
Accession No. NM_002415;;

5'-TCAACTATTACGACATGAA-3' (SEQ ID NO: 21)
(i.e., nucleotides 387-406 of GENBANK®
Accession No. NM_002415;;

5'-CAACTATTACGACATGAAC-3' (SEQ ID NO: 22)
(i.e., nucleotides 388-406 of GENBANK®
Accession No. NM_002415;;

5'-ACTATTACSEQ ID NO: 23)GACATGAACGC-3' (SEQ ID NO: 23)
(i.e., nucleotides 390-408 of GENBANK®
Accession No. NM_002415;;

5'-ACAACTCCACCTTCGCCTA-3' (SEQ ID NO: 24)
(i.e., nucleotides 426-444 of GENBANK®
Accession No. NM_002415;;

5'-CAACTCCACCTTCGCCTAA-3' (SEQ ID NO: 25)
(i.e., nucleotides 427-445 of GENBANK®
Accession No. NM_002415;;
or 5'-CCTTCTGGTGGGGAGAAAT-3' (SEQ ID NO: 26)
(i.e., nucleotides 527-545 of GENBANK®
Accession No. NM_002415;.

It is further provided that if the biological activity of a non-human MIF polypeptide is to be modulated, antisense modulators can be designed based on the nucleotide sequence of MIF from the appropriate organism. Several such nucleotide sequences are present in the GENBANK® database including, but not limited to GENBANK® Accession Nos. NM_001032915 (*Macaca mulatta*; amino acid Accession No. NP_001028087), NM_001033608 (*Bos taurus*; amino acid Accession No. NP_001028780), NM_001078655 (*Ovis aries*; amino acid Accession No. NP_001072123), NM_001077213 (*Sus scrofa*; amino acid Accession No. NP_001070681), NM_031051 (*Rattus norvegicus*; amino acid Accession No. NP_112313), NM_010798 (*Mus musculus*; amino acid Accession No. NP_034928), and XM_001489611 (*Equus caballus*; amino acid Accession No. XP_001489661).

The term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of an siRNA or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

The term "antisense polynucleotide" can refer to "small interfering RNA", "short interfering RNA", "small hairpin RNA", "siRNA", and "shRNA", which are used interchangeably and refer to any nucleic acid molecule capable of mediating RNA interference (RNAi) or gene silencing. See e.g., Bass, 2001; Elbashir et al., 2001b; and PCT International Publication Nos. WO 99/07409, WO 99/32619, WO 2000/01846, WO 2000/44895, WO 2000/44914, WO 2001/29058, and WO 2001/36646.

In some embodiments, the antisense polynucleotide is an siRNA and comprises a double stranded polynucleotide molecule comprising complementary sense and antisense regions, wherein the antisense region comprises a sequence complementary to a region of a target nucleic acid molecule such that when allowed to hybridize to the target nucleic acid molecule, the siRNA binds with specificity to the target nucleic acid molecule. In some embodiments, the target nucleic acid molecule is encodes a human MIF gene product (e.g., comprises nucleotides 98-445 of SEQ ID NO: 1 and/or encodes a polypeptide comprising an amino acid sequence as set forth in SEQ ID NO: 2). In some embodiments, the antisense region is the reverse complement of one of SEQ ID NOs: 3-26 (including such optional modification as described herein).

In some embodiments, the siRNA comprises a single stranded polynucleotide having self-complementary sense and antisense regions, wherein the antisense region comprises a sequence complementary to a region of a target nucleic acid molecule. In another embodiment, the siRNA comprises a single stranded polynucleotide having one or more loop structures and a stem comprising self-complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

The presently disclosed subject matter takes advantage of the ability of short, double stranded RNA molecules to cause the down regulation of cellular genes, a process referred to as RNA interference. As used herein, "RNA interference" (RNAi) refers to a process of sequence-specific post-transcriptional gene silencing mediated by a small interfering RNA (siRNA). See generally Fire et al., 1998. The process of post-transcriptional gene silencing is thought to be an evolutionarily conserved cellular defense mechanism that has evolved to prevent the expression of foreign genes (Fire, 1999).

RNAi might have evolved to protect cells and organisms against the production of double stranded RNA (dsRNA) molecules resulting from infection by certain viruses (particularly the double stranded RNA viruses or those viruses for which the life cycle includes a double stranded RNA intermediate) or the random integration of transposon elements into the host genome via a mechanism that specifically degrades single stranded RNA or viral genomic RNA homologous to the double stranded RNA species.

The presence of long dsRNAs in cells stimulates the activity of the enzyme Dicer, a ribonuclease III. Dicer catalyzes the degradation of dsRNA into short stretches of dsRNA referred to as small interfering RNAs (siRNA) (Bernstein et al., 2001). The small interfering RNAs that result from Dicer-mediated degradation are typically about 21-23 nucleotides in length and contain about 19 base pair duplexes. After degradation, the siRNA is incorporated into an endonuclease complex referred to as an RNA-induced silencing complex (RISC). The RISC is capable of mediating cleavage of single stranded RNA present within the cell that is complementary to the antisense strand of the siRNA duplex. According to Elbashir et al., cleavage of the target RNA occurs near the middle of the region of the single stranded RNA that is complementary to the antisense strand of the siRNA duplex (Elbashir et al., 2001a).

RNAi has been described in several cell types and organisms. Fire et al. described RNAi in *C. elegans* (Fire et al., 1998). Wianny & Zernicka-Goetz disclose RNAi mediated by dsRNA in mouse embryos (Wianny & Zernicka-Goetz, 1999). Hammond et al. were able to induce RNAi in *Drosophila* cells by transfecting dsRNA into these cells (Hammond et al., 2000). They demonstrated the presence of RNAi in cultured mammalian cells including human embryonic kidney and HeLa cells by the introduction of duplexes of synthetic 21 nucleotide RNAs (Elbashir et al., 2001b).

Other studies have indicated that a 5'-phosphate on the target-complementary strand of a siRNA duplex facilitate siRNA activity and that ATP is utilized to maintain the 5'-phosphate moiety on the siRNA (Nykanen et al., 2001). Other modifications that might be tolerated when introduced into an siRNA molecule include modifications of the sugar-phosphate backbone or the substitution of the nucleoside with at least one of a nitrogen or sulfur heteroatom (PCT International Publication Nos. WO 2000/44914 and WO 2001/68836) and certain nucleotide modifications that might inhibit the activation of double stranded RNA-dependent protein kinase (PKR), specifically 2'-amino or 2'-O-methyl nucleotides, and nucleotides containing a 2'-O or 4'-C methylene bridge (Canadian Patent Application No. 2,359,180).

Other references disclosing the use of dsRNA and RNAi include PCT International Publication Nos. WO 2001/75164 (in vitro RNAi system using cells from *Drosophila* and the use of specific siRNA molecules for certain functional genomic and certain therapeutic applications); WO 2001/36646 (methods for inhibiting the expression of particular genes in mammalian cells using dsRNA molecules); WO 99/32619 (methods for introducing dsRNA molecules into cells for use in inhibiting gene expression); WO 2001/92513 (methods for mediating gene suppression by using factors that enhance RNAi); WO 2002/044321 (synthetic siRNA constructs); WO 2000/63364 and WO 2001/04313 (methods and compositions for inhibiting the function of polynucleotide sequences); and WO 2002/055692 and WO 2002/055693 (methods for inhibiting gene expression using RNAi), each of which are incorporated herein by reference in their entireties.

In some embodiments, the presently disclosed subject matter utilizes RNAi to at least partially inhibit expression of MIF. Inhibition is preferably at least about 10% of normal expression amounts. In some embodiments, the method comprises contacting a target cell with an antisense polynucleotide in an amount sufficient to inhibit expression of MIF. In some embodiments, the target cell is present in a subject, and the RNA is introduced into the subject.

The RNA can have a double-stranded region comprising a first strand comprising a ribonucleotide sequence that corresponds to the coding strand of the gene encoding the target protein (e.g., MIF) and a second strand comprising a ribonucleotide sequence that is complementary to the first strand.

The first strand and the second strand hybridize to each other to form the double-stranded molecule. The double stranded region can be at least 15 basepairs in length, and in some embodiments, between 15 and 50 basepairs in length, and in some embodiments the double stranded region is between 15 and 30 basepairs in length.

In some embodiments, the RNA comprises one strand that forms a double-stranded region by intramolecular self-hybridization, which is preferably complementary over at least 19 bases. In some embodiments, the RNA comprises two separate strands that form a double-stranded region by intermolecular hybridization that is complementary over at least 19 bases.

One skilled in the art will recognize that any number of suitable common techniques can be used to introduce the RNAs into a target cell. In some embodiments, a vector encoding the RNA is introduced to the target cell. For example, the vector encoding the RNA can be transfected into the target cell and the RNA is then transcribed by cellular polymerases.

In some embodiments, a recombinant virus comprising a nucleic acid encoding the RNA can be produced. Introducing the RNA into a target cell then comprises infecting the target cell with the recombinant virus. Cellular polymerases transcribe the RNA resulting in expression of the RNA within the target cell. Engineering recombinant viruses is well known to those having ordinary skill in the art. One of skill would readily appreciate the multiple factors involved in selecting the appropriate virus and vector components needed to optimize recombinant virus production for use with the presently disclosed subject matter without the necessity of further detailed discussion herein. Details of recombinant virus production and use can be found in published PCT Patent Application Publication No. WO 2003/006477, herein incorporated by reference in its entirety. Alternatively, a commercial kit for producing recombinant viruses can be used, such as for example, the pSILENCER ADENO 1.0-CMV SYSTEM™ (Ambion, Austin, Tex., United States of America).

III.C. Anti-MIF Antibodies

In some embodiments, a modulator of MIF biological activity comprises an antibody that binds (in some embodiments, which specifically binds) to a MIF polypeptide, a MIF receptor polypeptide (e.g., CD74; Leng et al., 2003), and/or the CXC-chemokine receptors CXCR2 and CXCR4), or combinations thereof to thereby modulate a MIF biological activity. Anti-MIF antibodies, and compositions comprising the same, can be produced routinely by one of ordinary skill in the art after consideration of the instant disclosure. Additional such antibodies and compositions are disclosed in U.S. Pat. Nos. 6,645,493 and 7,517,523, both to Bucala et al., the disclosures of which are incorporated herein in their entireties.

As used herein, the term "antibody" refers to an immunoglobulin protein, or a functional fragment thereof, including, but not limited to a polyclonal antibody, a monoclonal antibody, a chimeric antibody, a hybrid antibody, a single chain antibody, a mutagenized antibody, a humanized antibody, and antibody fragments that comprise an antigen binding site (also referred to as the paratop, which in some embodiments comprises an Fab fragment, an Fv fragment, etc.). In some embodiments, an antibody of the presently disclosed subject matter is a monoclonal antibody that binds to a MIF polypeptide and/or a MIF receptor polypeptide. As used herein, the phrase "functional fragment thereof" when used in the context of an antibody refers to a fragment of an antibody that includes at least one antibody binding domain, such that the functional portion thereof binds to the same antigen and/or epitope as would the complete antibody from which it was derived.

In some embodiments, the anti-MIF antibody is a humanize antibody. As used herein the phrase "humanized antibody" refers to an immunoglobulin or antibody that includes at least one humanized immunoglobulin or antibody chain (i.e., at least one humanized light or heavy chain). The phrases "humanized immunoglobulin chain" and "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" indicates that, when aligned to a human immunoglobulin or antibody amino sequence for comparison purposes, the region shares in some embodiments at least 80%, in some embodiments at least 85%, in some embodiments at least 90%, in some embodiments at least 95%, in some embodiments at least 97%, in some embodiments at least 98%, and in some embodiments 99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" refers to an immunoglobulin or antibody having an immunoglobulin or antibody sequence that is in some embodiments at least 80%, in some embodiments at least 85%, in some embodiments at least 90%, in some embodiments at least 95%, in some embodiments at least 97%, in some embodiments at least 98%, and in some embodiments 99% identical to that of a non-human organism, e.g., a non-human mammal.

Accordingly, all regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

Methods for producing antibodies, functional fragments thereof, single chain versions thereof (see e.g., PCT International Patent Application Publication No. WO 88/09344), chimeric versions thereof (see e.g., PCT International Patent Application Publication No. WO 89/09622), and humanized versions thereof (see e.g., U.S. Pat. Nos. 5,877,293; 5,886,152; and 6,054,297) are known to those of skill. In some embodiments, the antibody, fragment, or derivative thereof is labeled with a detectable label. Suitable detectable labels include but are not limited to radioactive labels and fluorescent labels.

IV. Methods of Use

The presently disclosed subject matter provides methods for modulating eye damage associated with a disease or disorder, and/or damage incident to ocular surgery or other traumatic event to the eye, the method comprising administering to a subject an effective amount of a modulator of a macrophage migration inhibitory factor (MIF) polypeptide biological activity. Therapeutic methods disclosed herein include, but are not limited to methods for treating dry macular degeneration, wet macular degeneration, retinopathy of prematurity, background diabetic retinopathy, proliferative diabetic retinopathy, sickle cell retinopathy and other vasoproliferative retinopathies, intraocular scarring (including, but not limited to proliferative vitreoretinopathy), autoimmune uveitis, autoimmune uveoretinitis, uveitis of various etiologies, dry eye syndrome with and without Sjogren's syndrome, blunt or perforating ocular trauma and related ocular pathologies, open angle glaucoma, and secondary glaucoma in a subject. The presently disclosed subject matter also provides methods for modulating the severity of, delaying the onset of, and/or inhibiting and/or preventing the development of an ocular disease, and methods for modulating the severity of, delaying the onset of, and/or inhibiting and/or preventing the development of scarring and/or other consequence of wound healing incident to ocular surgery, as well as modulating the behavior of intra- or extraocularly grafted cell transplants that are used to reconstruct deranged ocular tissues and/or treat ocular diseases using tissue engineering methods.

With respect to the therapeutic methods of the presently disclosed subject matter, a "subject" as the term is used herein in some embodiments refers to a vertebrate subject. An exemplary vertebrate is warm-blooded, an exemplary warm-blooded vertebrate is a mammal, and an exemplary mammal is a human. As used herein, the term "subject" includes both human and animal subjects. Thus, veterinary therapeutic uses are provided in accordance with the presently disclosed subject matter.

As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like. Additionally, the treatment of animals employed in a research context including, but not limited to mice, rats, and other mammals such as primates, is also provided.

The modulators of the presently disclosed subject matter can be employed in pharmacological compositions for the treatment and/or prevention of many diseases and disorders associated with MIF biological activities. A compound of the presently disclosed subject matter can be administered to a subject (e.g., a human subject) by itself or in pharmaceutical compositions where it is mixed with suitable carriers or excipients at doses to treat or ameliorate various conditions associated with MIF biological activities. An effective dose (e.g., a therapeutically effective dose) refers to that amount of the compound sufficient to modulate a MIF biological activity, it being understood that such modulation can occur at different concentrations such that a person skilled in the art could determine the required dosage of compound to modulate the target MIF biological activity. Effective doses can be administered alone or as adjunctive therapy in combination with other treatments for the indications disclosed herein. Techniques for the formulation and administration of the compounds of the presently disclosed subject matter can be found in the latest edition of *Remington's Pharmaceutical Sciences*, Mack Publishing Co., Easton, Pa., United States of America.

Suitable methods for administering to a subject a therapeutic compound in accordance with the methods of the present subject matter include but are not limited to systemic administration, parenteral administration (including intravascular, intramuscular, intraarterial administration), oral delivery, buccal delivery, subcutaneous administration, inhalation, intratracheal installation, surgical implantation, transdermal or transconjunctival delivery, periocular or retrobulbar injections, intraocular administration (e.g., by injection or delivery through a slow release device), and hyper-velocity injection/bombardment.

The pharmaceutical compositions and compounds of the presently disclosed subject matter can be manufactured in a manner that is itself known, e.g., by conventional mixing, dissolving, dragee-making, levitating, emulsifying, encapsulating, entrapping, and/or lyophilizing processes. Pharmaceutical compositions for use in accordance with the presently disclosed subject matter can thus be formulated in any conventional manner using one or more physiologically acceptable carriers comprising excipients and auxiliaries that facilitate processing of the active compounds into preparations, which can be used pharmaceutically (e.g., that can be administered to a human). As would be understood by those of skill, proper formulation can be dependent upon the route of administration chosen.

For injection, the compounds of the presently disclosed subject matter can be formulated in aqueous solutions, in some embodiments in physiologically compatible buffers, such as but not limited to Hank's solution, Ringer's solution, or physiological saline buffer. A therapeutic composition as described herein can thus comprise a composition that includes a pharmaceutically acceptable carrier. Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

For transmucosal administration, penetrants appropriate to the barrier to be permeated can be used in the formulation. Such penetrants are known in the art.

For oral administration, a pharmaceutical composition can be formulated readily by combining a modulator of the presently disclosed subject matter with pharmaceutically acceptable carriers well known to those in the art. Such carriers facilitate the formulation of the compounds of the presently disclosed subject matter as tablets, pills, dragees, capsules, liquids, gels, syrups, slurries, suspensions, and the like, for oral ingestion by a patient to be treated. Pharmaceutical preparations for oral use can be obtained by combining a modulator of the presently disclosed subject matter with a solid excipient, optionally grinding the resulting mixture, and processing the mixture of granules, after adding suitable auxiliaries, if desired, to obtain tablets or dragee cores. Exemplary suitable excipients are, in particular, fillers including but not limited to sugars, including lactose, sucrose, mannitol, or sorbitol; cellulose preparations including but not limited to maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, including but not limited to the cross-linked polyvinyl pyrrolidone, agar, alginic acid, or a salt thereof including but not limited to sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and/or suitable organic solvents or solvent mixtures. Dyestuffs or pigments can be added to the tablets or dragee coatings for identification and/or to characterize different combinations of active compound doses.

Pharmaceutical preparations that can be used orally include but are not limited to push-fit capsules made of gelatin, as well as soft, sealed capsules made of gelatin and a plasticizer, such as glycerol or sorbitol. The push-fit capsules can contain the modulator of the presently disclosed subject matter in admixture with filler including but not limited to lactose, binders including but not limited to starches, and/or lubricants including but not limited to talc or magnesium stearate and, optionally, stabilizers. In soft capsules, the active compounds can be dissolved or suspended in suitable liquids, including but not limited to fatty oils, liquid paraffin, and/or liquid polyethylene glycols. In addition, stabilizers can be added. In some embodiments, formulations for oral administration are in dosages suitable for such administration.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

For buccal administration, the compositions of the presently disclosed subject matter can take the form of tablets or lozenges formulated in conventional manner.

For administration by inhalation, the compositions for use according to the presently disclosed subject matter can in some embodiments be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, and/or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the composition and a suitable powder base such as lactose or starch.

The modulators of the presently disclosed subject matter can be formulated for parenteral administration by injection, e.g., by bolus injection or continuous infusion. Formulations for injection can be presented in unit dosage form, e.g., in ampoules or in multi-dose containers, optionally with an added preservative. The compositions can take forms such as, but not limited to suspensions, solutions, or emulsions in oily or aqueous vehicles, and can ay contain formulatory agents such as suspending, stabilizing, and/or dispersing agents.

Pharmaceutical formulations for parenteral administration include in some embodiments aqueous solutions of the modulators of the presently disclosed subject matter in water-soluble form. Additionally, suspensions of the active compounds can be prepared in dimethylsulfoxide (DMSO) or as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances designed to increase the viscosity of the suspension, such as but not limited to sodium carboxymethyl cellulose, sorbitol, and/or dextran. Optionally, the suspension can also contain suitable stabilizers or agents that increase the solubility of the compounds to allow for the preparation of highly concentrated solutions.

Alternatively, the modulators of the presently disclosed subject matter can be provided in powder form for constitution with a suitable vehicle, e.g., sterile pyrogen-free water, before use.

The modulators of the presently disclosed subject matter can also be formulated in rectal compositions such as suppositories or retention enemas, e.g., containing conventional suppository bases such as cocoa butter or other glycerides.

In addition to the formulations described previously, the modulators of the presently disclosed subject matter can also be formulated as a depot preparation. Such long acting formulations can be administered by implantation (for example subcutaneously or intramuscularly) or by intramuscular injection. Thus, for example, the modulators of the presently disclosed subject matter can be formulated with suitable polymeric or hydrophobic materials (for example, as an emulsion in an acceptable oil) or ion exchange resins, or as sparingly soluble derivatives, for example, as a sparingly soluble salt.

For example, a modulator of the presently disclosed subject matter can be provided in a drug delivery system (e.g., an intraocular delivery system), for example in a liposome, a nanoparticle, or an emulsion.

Liposomes and emulsions are well known examples of delivery vehicles or carriers for hydrophobic drugs. Certain organic solvents such as DMSO also can be employed, although usually at the cost of greater toxicity. Additionally, the modulators of the presently disclosed subject matter can be delivered using a sustained-release system, such as but not limited to semipermeable matrices of solid hydrophobic polymers containing the therapeutic agent. Various forms of sustained-release materials have been established and would be known to those skilled in the art after review of the instant disclosure. Sustained-release capsules can, depending on their chemical nature, be formulated to release the compounds over a few days, few weeks, or months. Depending on the chemical nature and the biological stability of the therapeutic reagent, additional strategies for protein stabilization can be employed.

The compositions of the presently disclosed subject matter can also be formulated in complex with a pharmaceutically acceptable liposome or nanoparticle. In some embodiments, the compositions are provided in a form acceptable for direct or indirect administration to the eye, optionally for application to an external surface of the eye. In some embodiments, the compositions comprise a liposome and/or a nanoparticle in which the modulator is encapsulated and/or attached, optionally wherein the liposome and/or the nanoparticle comprises a targeting ligand that targets the liposome and/or the nanoparticle to the eye or a structure within the eye. In some embodiments, the nanoparticles are constructed from one or more biocompatible polymers, one or more biodegradable polymers, or both. In some embodiments, the at least one of the one or more biodegradable polymers is selected from the group consisting of poly(lactic acid) (PLA), poly(glycolic acid) (PGA), polycaprolactone (PCL), a copolymer of lactic acid and glycolic acid (PLGA), a copolymer of lactic acid and caprolactone, polyepsilon caprolactone, polyhyroxy butyric acid, a poly(ortho)ester, a polyurethane, a polyanhydride, a polyacetal, a polydihydropyran, and a polycyanoacrylate. By way of example and not limitation, compositions and methods for employing nanoparticles to be directly administered to the eye by injection into the sclera of the eye applicants respectfully disclosed in U.S. Pat. No. 7,648,959 to Bender et al., which is incorporated by reference in its entirety.

As such, the compositions of the presently disclosed subject matter can also be formulated for intraocular delivery. As used herein, the phrase "intraocular delivery" refers to delivery of an active agent (including, but not limited to an active agent that modulates a biological activity of a MIF-1 polypeptide in a subject, particularly a biological activity of a MIF-1 polypeptide present in the eye of a subject) to the ocular region or an ocular site of a subject. As used herein, an "ocular region" or "ocular site" refers generally to any area of the eyeball, including the anterior and posterior segment of the eye, and which generally includes, but is not limited to, any functional (e.g., for vision) or structural tissues (e.g., the retina or surrounding areas) found in the eyeball, or tissues or cellular layers that partly or completely line the interior or exterior of the eyeball. Exemplary, non-limiting ocular regions or sites include the anterior chamber, the posterior chamber, the vitreous cavity, the choroid, the suprachoroidal space, the subretinal space, the conjunctiva, the subconjunctival space, the episcleral space, the intracorneal space, the epicorneal space, the sclera, the pars plana, surgically-induced avascular regions, the macula, and the retina.

Similarly, the phrase "intraocular delivery system" as used herein refers to a device or element that is structured, sized, or otherwise configured to be placed in an eye. In some embodiments, an intraocular delivery system is generally biocompatible with physiological conditions of an eye and does not cause unacceptable or undesirable adverse side effects. In some embodiments, intraocular delivery systems can be placed in an eye without disrupting vision of the eye. By way of example and not limitation, an intraocular delivery system can be in the form of a plurality of particles, such as microparticles, or can be in the form of implants. Intraocular delivery systems can also include a polymeric component. Exemplary, non-limiting intraocular delivery systems are described, for example, in U.S. Pat. Nos. 5,466,233; 7,678,078; 7,883,717; 7,887,508; and 7,931,909; the disclosure of each of which is incorporated herein by reference in its entirety.

The presently disclosed compositions can be administered to a subject in any form and/or by any route of administration. In some embodiments, the formulation is a sustained release formulation, a controlled release formulation, or a formulation designed for both sustained and controlled release. As used herein, the term "sustained release" refers to release of an active agent such that an approximately constant amount of an active agent becomes available to the subject and/or to a specific site in the subject over time. The phrase "controlled release" is broader, referring to release of an active agent over time that might or might not be at a constant level. Particularly, "controlled release" encompasses situations and formulations where the active ingredient is not necessarily released at a constant rate, but can include increasing release over time, decreasing release over time, and/or constant release with one or more periods of increased release, decreased release, or combinations thereof. Thus, while "sustained release" is a form of "controlled release", the latter also includes delivery modalities that employ changes in the amount of an active agent (e.g., a modulator of a MIF-1 biological activity) that are delivered at different times. The compositions of the presently disclosed subject matter can also comprise suitable solid- or gel-phase carriers and/or excipients. Representative examples of such carriers and/or excipients include, but are not limited to calcium carbonate, calcium phosphate, various sugars, starches, cellulose derivatives, gelatin, and polymers such as polyethylene glycols.

Many of the modulators of the presently disclosed subject matter identified can be provided as salts with pharmaceutically compatible counterions. Pharmaceutically compatible salts can be formed with many acids, including but not limited to hydrochloric, sulfuric, acetic, lactic, tartaric, malic, succinic, etc.; or bases. Salts tend to be more soluble in aqueous or other protonic solvents than are the corresponding free base forms. Examples of pharmaceutically acceptable salts, carriers, and/or excipients would be well known to those skilled in the art after review of the instant disclosure, and can also be found, for example, in *Remington's Pharmaceutical Sciences*, 18th Edition, (1990) Gennaro (ed.) Mack Publishing Co., Easton, Pa., United States of America. Such salts include, but are not limited to, sodium, potassium, lithium, calcium, magnesium, iron, zinc, hydrochloride, hydrobromide, hydroiodide, acetate, citrate, tartrate, and malate salts, and the like.

Pharmaceutical compositions suitable for use in the presently disclosed subject matter include compositions wherein the modulators of the presently disclosed subject matter are contained in an effective amount to achieve their intended purpose. More specifically, the phrase "therapeutically effective amount" refers to an amount of a modulator of the presently disclosed subject matter effective to prevent or inhibit development and/or progression of a condition associated with a MIF biological activity in a subject being treated, and/or to reduce or eliminate a symptom associated therewith. Determination of an effective amount of a modulator of the presently disclosed subject matter would be well within the capability of those skilled in the art, especially in light of the detailed disclosure provided herein.

For any modulator used in the methods of the presently disclosed subject matter, the therapeutically effective dose can be estimated initially from tautomerase inhibition assays and cell culture assays. Such information can be used to more accurately determine useful doses in humans. Exemplary methods for assaying tautomerase activities are disclosed in U.S. Pat. No. 6,492,428 and references cited therein, the disclosures of which are incorporated herein by reference in their entireties.

As such, a therapeutically effective dose is that amount of a modulator of the presently disclosed subject matter that results in a reduction in the development or severity of a disease associated with a MIF biological activity. Toxicity and therapeutic efficacy of such compounds can be determined by standard pharmaceutical, pharmacological, and/or toxicological procedures in vitro and/or in vivo (e.g., in cell culture and/or experimental animals). For example, $LD_{50}$ (the dose lethal to 50% of the population) and $ED_{50}$ (the dose therapeutically effective in 50% of the population) values for a given modulator or mixture of modulators can be determined. The dose ratio between toxic and therapeutic effects is the therapeutic index and it can be expressed as the ratio between $LD_{50}$ and $ED_{50}$. In some embodiments, modulators that exhibit high therapeutic indices are employed. The data obtained from cell culture assays and/or animal studies can be used in formulating a range of dosages for use in subjects (in some embodiments, human subjects). The dosages of such modulators lie in some embodiments within a range of circulating concentrations that include the $ED_{50}$ (or the $ED_{99}$) with little or no toxicity. In some embodiments, the dosages can vary within this range depending upon the dosage form employed and the route of administration utilized. In some embodiments, the exact formulation(s), route(s) of administration, and/or dosage(s) for any given modulator can be chosen by the individual physician in view of the subject's condition.

Dosage amount and interval can be adjusted individually to provide systemic and/or localized levels of the modulator of the presently disclosed subject matter that are sufficient to maintain the desired modulating effects, or minimal effective concentration (MEC). The MEC can vary for each modulator but can be estimated from in vitro data: e.g., the concentration necessary to achieve a 50-97% inhibition of MIF activity. Dosages necessary to achieve the MEC can depend on individual characteristics and route of administration. However, HPLC assays, bioassays, and/or immunoassays can be used to determine systemic and/or localized concentrations.

Dosage intervals can also be determined using the MEC value. A modulator of the presently disclosed subject matter can be administered using a regimen that maintains plasma levels above the MEC for in some embodiments 10-90% of a treatment phase, in some embodiments between 30-90% of a treatment phase, and in some embodiments between 50-90% of a treatment phase.

In cases of local administration for instance, direct introduction into a target organ or tissue, or selective uptake, can cause the effective local concentration of a modulator of the presently disclosed subject matter to be unrelated to plasma concentration.

The amount of a modulator of the presently disclosed subject matter administered can, of course, be dependent on the subject being treated, on the subject's weight, the severity of the affliction, the manner of administration, and/or the judgment of the prescribing physician.

The modulators of the presently disclosed subject matter can, if desired, be presented in a pack or dispenser device that contains one or more unit dosage forms containing the modulator. The pack can, for example, comprise a metal or plastic foil, such as a blister pack. The pack or dispenser device can in some embodiments be accompanied by instructions for administration. Compositions comprising a modulator of the presently disclosed subject matter formulated in a compatible pharmaceutical carrier can also be prepared, placed in an appropriate container, and labeled for treatment of an indicated condition.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Inhibition of Subretinal Choroidal Neovascularization with a Small Molecule MIF Inhibitor In order to test the efficacy of MIF inhibitors to prevent subretinal or intraretinal neovascularization, subretinal choroidal neovascularization (CNV) was induced in C57BL/6 mice (n=3; 6 eyes/per experimental group) using a double-frequency YAG laser (532 nm). Laser parameters were 600 mW of power, 0.1 sec duration, and a spot size of 50 micrometers. Approximately 8-12 spots per eye were placed. One group of animals received 500 micrograms of 4-(2-fluorophenyl)-6-iodopyrimidine (Compound 1) into the posterior sub-tenon space through a 32-G needle 24 hours before laser application. Compound 1 was dissolved in 1:1 mixture of DMSO and corn oil solvent. The injection volume was 5 microliters.

Another group of animals received the drug six days after the laser photocoagulation when subretinal neovascularization is at its maximum growth. This scenario exemplified the use of MIF inhibitors (including, but not limited to Compound 1) in the treatment of active wet age-related macular degeneration (AMD). The two positive controls received either PBS or DMSO:corn oil mixture into the subTenon space. $MIF^{-/-}$ animals (i.e., mice with a homozygous knock out of the MIF gene) were also taken as the negative control.

Ten days after the laser photocoagulation animals were perfused with high molecular weight dextran (2 megadalton)-conjugated fluorescein under deep anesthesia and then sacrificed. Choroidal neovascularization (CNV) yield (=percent of the spots with CNV) was determined under a fluorescent microscope.

As shown in FIG. 1, both pre-(4th bar) and post-laser (5th bar) application of Compound 1 significantly suppressed the occurrence of CNV. This effect was comparable to knocking out MIF completely (3rd bar).

Figure 2:
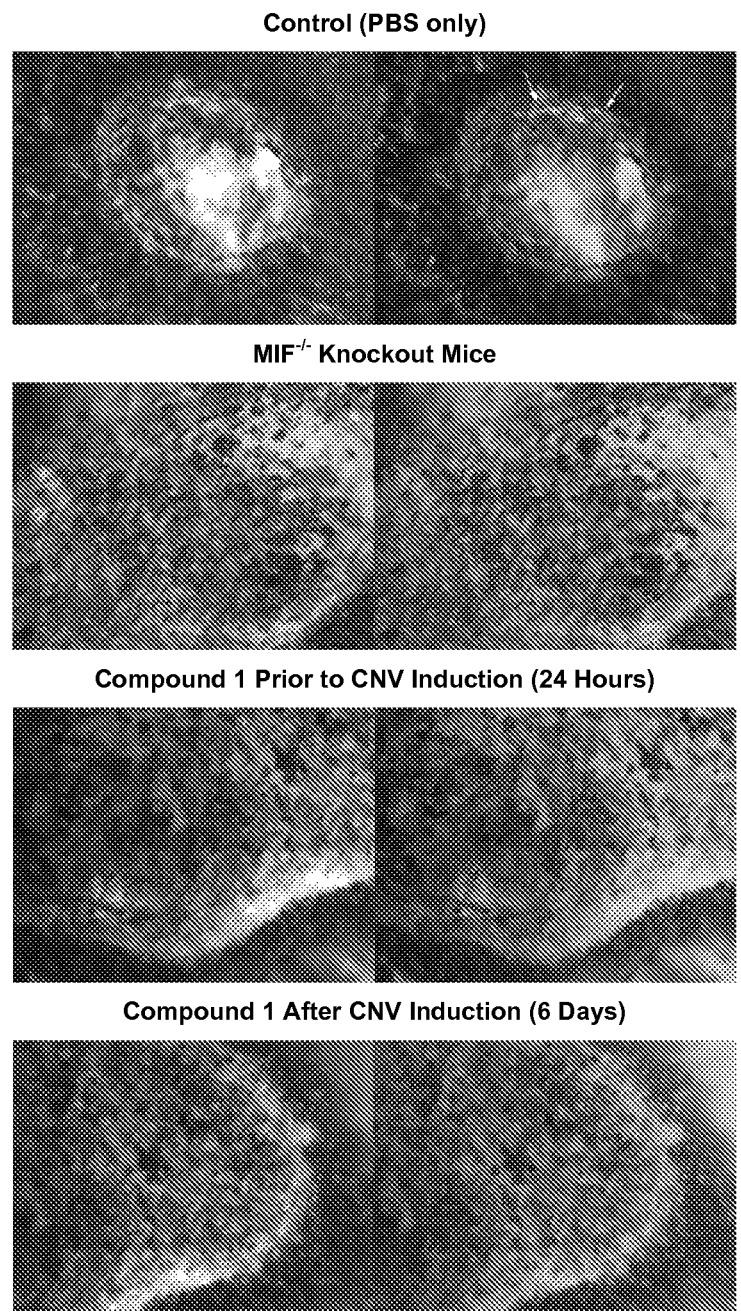
FIG. 2 depicts a series of fluorescence micrographs of eyes induced to undergo subretinal choroidal neovascularization (CNV) under various treatment conditions. The green fluorescence depicted corresponds to locations where high molecular weight dextran-conjugated fluorescein accumulates, which is indicative of sites of CNV.

Although it is not presently desired to be bound by any particular mechanism of action, FIG. 2 provides evidence of a potential mechanism of action. In the control animals, neighboring RPE cells could not populate the laser spot (see FIG. 2).

Figure 3:
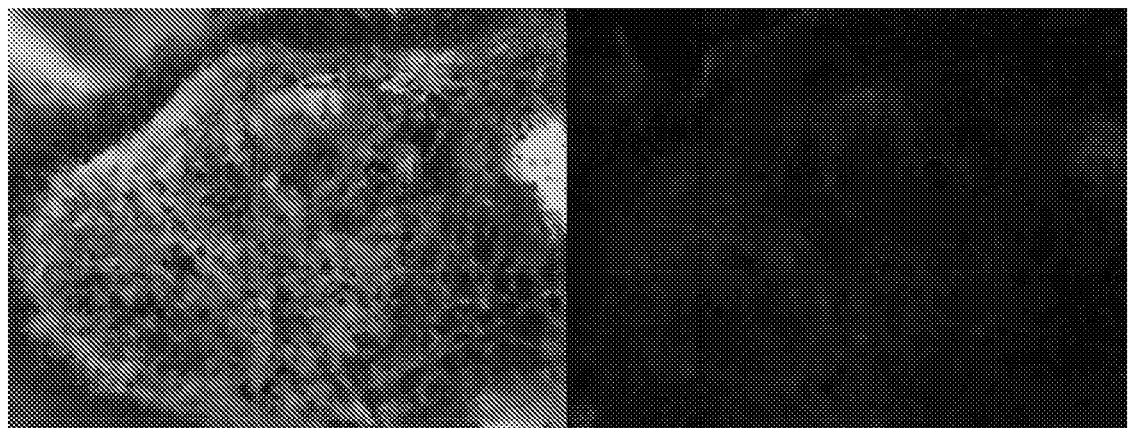
FIG. 3 depicts fluorescence micrographs of a representative site of a laser spot. The panel on the left shows the cellular proliferation over the laser spot that almost covered the whole spot area. Some of these cells contained pigment indicating that they were retinal pigment epithelial (RPE) cells. The panel on the right demonstrates that the cells resurfacing the laser spot were retinal pigment epithelial (RPE) cells since these cells stained positive with an antibody specific for the RPE marker RPE65.

RPE cells are attachment-dependent cells and require an intact matrix to grow on. Once laser is applied, Bruch's membrane was coagulated and adjacent cells could not proliferate to cover the spot. Absence of RPE resulted in a gap through which neovascular vessels entered the subretinal space (white arrows in top panel). In the cases of MIF$^{-/-}$ knockout mice or in animals that were treated with Compound 1, RPE cells proliferated to cover the spot. It was determined that the cells covering the spot were RPE cells because they expressed the RPE marker RPE65 (see FIG. 3).

Covering the spot RPE did not allow any neovascular epithelia to grow into the subretinal space. This is a natural way of suppressing choroidal neovascularization. It is a known fact that when CNV burns out naturally, it occurs in eyes where RPE cells undergo proliferation. Fas-FasL-induced apoptotic cell death of neovascular epithelia has been identified as one of the mechanisms responsible for this phenomenon, although it is not presently desired to be bound by any particular mechanism of action.

This has several implications. For example, there are no drugs that currently are known to work through this mechanism. Current drugs for the treatment of exudative AMD all aim to destroy new vessel formation or alter the permeability of new vessels by targeting vascular endothelial growth factor (VEGF) mediated signal transduction (e.g., through VEGF receptors, VEGF itself, and/or downstream signaling molecules), integrins, platelet-derived growth factor (PDGF), etc. The systemic absorption of these drugs can be a concern since angiogenesis is required for coronary and cerebral collateral formation especially in the aged group patients suffering from AMD.

In the case of MIF blockage lack of an anti-angiogenic effect automatically eliminates such potential vascular side effects (e.g., MI or CVA). Also, current agents are given as intravitreal injections which are uncomfortable to patients and carry several inherent risks such as retinal detachment, intravitreal bleeding, and/or endophthalmitis. However, Compound 1 and related molecules are lipophilic and can diffuse through sclera without difficulty. This will facilitate the deposit of comparatively larger amounts of drug into the subTenon space of patients with less discomfort and danger to the patient.

Another unexpected observation was the ability of RPE to grow over the laser spots. RPE cells appeared to increase in density and to assume their typical differentiated hexagonal morphology at the end of the observation period. Epithelial differentiation of RPE was also evident by the expression of RPE-specific cell marker, RPE65. Since MIF neutralization allowed RPE to populate bare areas without the presence of a previously established matrix, the present observation provides evidence that MIF neutralization is expected to be useful for treating geographic atrophy (i.e., dry AMD) as well. Considering that 1.6 million people have geographic atrophy and 200,000 every year are added to this pool, the importance of this observation is clear.

And finally, the only drug presently available to avoid the development of exudative AMD (see the 4th bar of FIG. 1) is high-dose antioxidants and vitamins (AREDS formula: vitamins C, E, beta carotene, and zinc). 8 million people in the United States alone above the age of 55 are at high risk of developing advanced AMD, and 1.3 million of them will in fact develop this condition. Currently, all such individuals are being advised to take these vitamins daily with the hope of saving about 25% of them from the condition. The cost of these vitamins is approximately $960 million per year for a benefit that is arguably not even a fraction of what was observed in the studies disclosed herein.

It will be understood that various details of the presently disclosed subject matter may be changed without departing from the scope of the presently disclosed subject matter. Furthermore, the foregoing description is for the purpose of illustration only, and not for the purpose of limitation.

Example 2

Effect of MIF Neutralization on RPE Differentiation and Wound Healing

The effect of MIF neutralization on retinal pigment epithelial (RPE) differentiation and wound healing properties in animal models of chemical RPE debridement and laser-induced choroidal neovascularization (CNV) was tested. CNV was induced in C57BL/6 mice (n=18) using a double-frequency YAG laser (532 nm; 600 mW; 0.1 sec; 50 μm; 8-12 spots/eye). The experimental group (n=6) received 500 μg/in 5 μl of a MIF inhibitor (4-iodo-6-(2-fluorophenyl)pyrimidine; Compound 1) in the posterior subtenon space 24 hours before laser application. Ten (10) days later, animals were sacrificed and induced CNV (i.e., yield) was determined.

Another group of animals received MIF-inhibitor 6 days after laser treatment to determine the effect of MIF-neutralization on established CNV. RPE loss was also mimicked in twelve C57BL/6 mice by patchy debridement of RPE using intraperitoneal sodium iodate injection (25 mg/kg). Seven days later, animals received the subtenon MIF inhibitor and RPE resurfacing was determined on day 21 by morphometric image analysis. In all experiments, MIF$^{-/-}$ animals and wild type animals that received the solvent (DMSO/Corn oil) and/or PBS were used as controls.

Immunostaining for RPE65, vimentin, E-cadherin, and N-cadherin was used to identify and characterize RPE differentiation. MIF-neutralization significantly lowered the CNV yield compared to the controls regardless of the application time; from 72.1% and 80% for PBS and the solvent, respectively, to 10.7% and 12.9% for pre- and post-laser (p=0.0001). This decrease was comparable to the CNV yield in MIF$^{-/-}$ animals (12.5%, p=0.76). MIF-neutralization also resulted in significantly higher surface coverage by RPE cells compared to controls (93.8±6.3% vs. 60.9±19.0%; p=0.001). Proliferating RPE cells in MIF-neutralized animals maintained differentiated cuboidal morphology and expressed E-cadherin and RPE-65.

Thus, MIF neutralization enhanced the ability of RPE cells to proliferate and maintain differentiated features. This resulted in the inhibition of CNV by rapid sealing of the damaged subretinal space and repopulation of the denuded Bruch's membrane.

Example 3

Prevention of PVR by MIF Neutralization Via Inhibition of EMT

To determine whether MIF inhibition can prevent the formation proliferative vitreoretinopathy (PVR) by inhibiting epithelio-mesenchymal transformation (EMT) of RPE, primary human RPE cells from two young donors (20 and 26 years old) were plated on tissue-culture plastic and maintained in DMEM H16 supplemented with 10% FBS and a MIF inhibitor (4-IPP; 25-50 μM) for 3 weeks. Control cells were exposed only to the solvent (DMSO/Corn oil).

Morphology and qPCR for microphthalmia transcription factor (MITF), plasminogen activator inhibitor type-1 (PAI-1), vimentin, and N-cadherin were used to assay for the presence of EMT.

The effect of MIF inhibition on EMT was further tested in vivo using an animal model of PVR. Six (6) adult C57BL/6 mice were anesthetized with pentobarbital sodium (70 mg/kg i.p.) and a linear incision was made in the cornea. The lens was removed and a tear was created in the peripheral retina using a 32G needle. The corneal incision was then sutured with 10-0 nylon.

The experimental group received 500 μg/in 5 μl of a MIF inhibitor (4-iodo-6-(2-fluorophenyl)pyrimidine; Compound 1) in the posterior subtenon space on Days 0 and 5, whereas control animals received the solvent. Animals were sacrificed on Day 10 and light microscopy was used to assess the presence and extent of PVR. MIF$^{-/-}$ animals (n=3) were also used as control.

Cultured human RPE cells treated with MIF-inhibitor were significantly fewer in number but maintained their typical cuboidal epithelial morphology, in contrast to control RPE, which acquired a fibroblast-like morphology. Consistent with the cell morphology, MIF neutralization resulted in the reduction of mRNA levels of mesenchymal markers (vimentin, 8.5×; PAI-1, 19.7×; and N-cadherin, 43.2×) and an increase in mRNA levels of the epithelial gene product, MITF (1.6×). In control eyes, surgically-induced retinal detachment was complicated with the formation of epi- and subretinal fibrotic membranes, as well as multilayering of the RPE cells. RPE cells remained as a monolayer in the experimental group that received MIF-inhibitor and in MIF$^{-/-}$ animals. Neutralization of MIF significantly inhibited the formation of peri-retinal membranes.

As such, MIF was shown to be an important regulator of EMT in RPE. Neutralization of MIF can thus be a potential therapeutic target for the prevention and treatment of ocular proliferative disorders such as PVR.

Example 4

EMT of RPE a Cause of Proliferative Vireoretinopathy (PVR)

Proliferative vitreoretinopathy is a major, if not the main, cause of the failure of the retinal detachment surgery. It is characterized by phonotypical and functional changes in RPE cells. They acquire a fibroblast-like morphology and start to form contractile periretinal membranes. Contraction of these epiretinal and subretinal membranes pull the retina away from the eye wall and result in retinal detachment.

Whether MIF is involved in the RPE wound healing response in the setting of retinal detachment and whether neutralization of MIF can reduce or eliminate the development of PVR was tested.

As a first step, the molecular signature of RPE mesenchymal transition in PVR was investigated. For this purpose, RNA was isolated from RPE from scar tissue recovered the eyes of PVR patients, and the mRNA levels of epithelial and mesenchymal gene products was compared to mRNA levels of these same gene products in RPE cells harvested from fresh (<24 hours) donor eyes using quantitative PCR (qPCR). In the setting of PVR, the mRNA level of the epithelial gene product microphthalmia transcription factor (MITF) in RPE was 3.8-fold lower than that in normal RPE cells. Additionally, the mesenchymal-associated gene products vimentin and PAI-1 were 17.7-fold and 287.9-fold higher, respectively, in PVR RPE vs. normal RPE.

Example 5

Effect of MIF Neutralization with 4-IPP on EMT of RPE Cells In Vitro

Human RPE cells were isolated freshly (<24 hours) from human donor eyes. Harvested RPE cells were cultured on tissue-culture plates. 25 μM of 4-IPP, a small molecule antagonist of MIF, was added to the culture medium every other day. Untreated wells were taken as control. 21 days later, cells were photographed and RNA was isolated for qPCR analyses.

Figure 4:
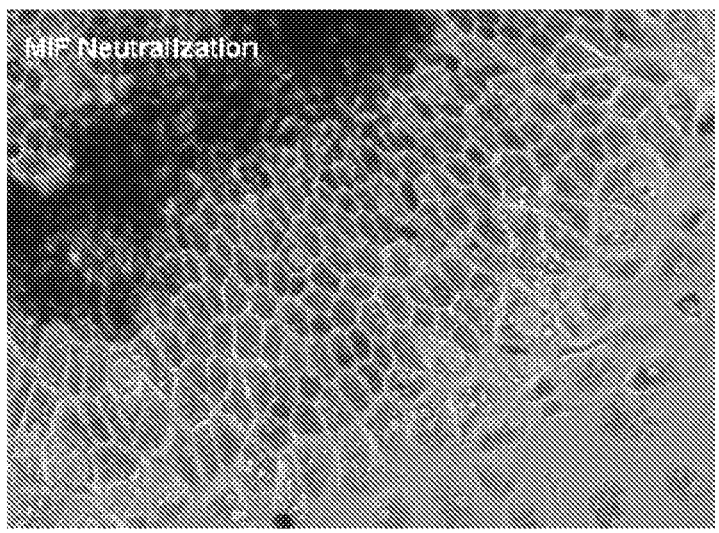
FIGS. 4A and 4B are photomicrographs of human RPE cells isolated from human donor eyes and cultured for 21 days on tissue-culture plates in the presence (FIG. 4A) or absence (FIG. 4B) of the small molecule MIF antagonist 4-iodo-6-phenylpyrimidine (4-IPP).
Figure 4:
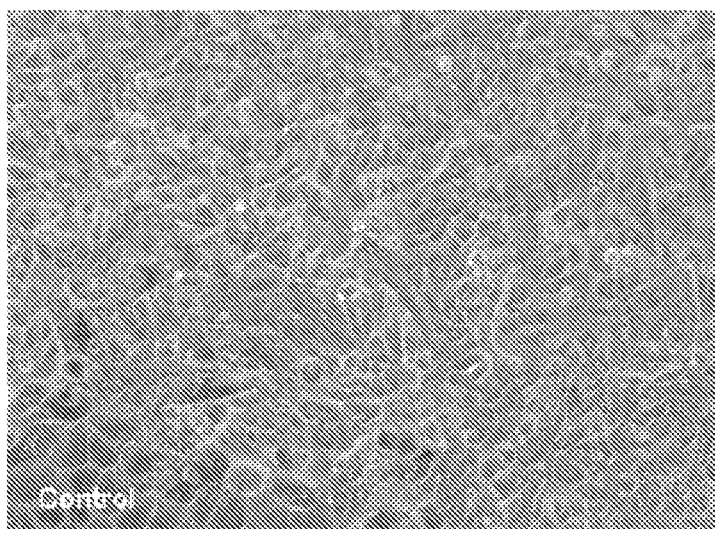

Cultured RPE cells treated with the MIF inhibitor (see FIG. 4A) were significantly fewer in number, were uniformly pigmented, retained a classical cuboidal epithelial morphology, and were generally restricted to individual, well pigmented, colonies. In stark contrast, vehicle control RPEs (see FIG. 4B) had proliferated well beyond individual colonies to cover the entirely of the wells, were largely de-pigmented, and most cells took on a fibroblast-like morphology. Consistent with an attenuation of EMT resulting from MIF inhibition, control treated RPE cells had 1.6-fold lower MITF mRNA levels than MIF inhibitor-treated RPE cells, while mesenchymal gene product levels were dramatically higher in control RPE cells than in MIF inhibitor-treated RPE cells. Specifically, control RPE cells had 8.5-fold, 19.7-fold, and 43.2-fold higher mRNA levels of vimentin, PAI-1, and N-cadherin, respectively, than the MIF inhibitor-treated cells.

Taken together, these results indicated that MIF was an important mediator of RPE EMT and thus represents an attractive target for therapeutic intervention in ocular diseases involving dysregulated differentiation of retinal pigmented epithelial monolayers.

Example 6

MIF Neutralization with a Small Molecule Inhibitor Inhibited the Formation of PVR In order to test the safety and efficacy of MIF neutralization in vivo, the model disclosed in Saika et al., 2004 was employed.

Briefly, retinal detachment was created in three C57BL6 mice. Animals underwent a lensectomy/vitrectomy procedure under ketamine/xylazine anesthesia. These procedures were done through a central slit corneal incision. After the completion of the procedure, a tear was created in the peripheral retina under the microscope and the sensory retina was detached. Next, the cornea was closed with a 10-0 nylon suture and each animal was returned to its cage. The experimental group received 500 μg/in 5 μl of the MIF inhibitor 4-(2-fluorophenyl)-6-iodopyrimidine (Compound 1) in the posterior subtenon space on days 0 and 5, whereas control animals received the solvent (i.e., a 1:1 mixture of DMSO and corn oil). Animals were sacrificed on day 10 and light microscopy was used to assess the presence and extent of PVR. MIF$^{-/-}$ knockout animals (n=3) were also used as a control.

Figure 5:
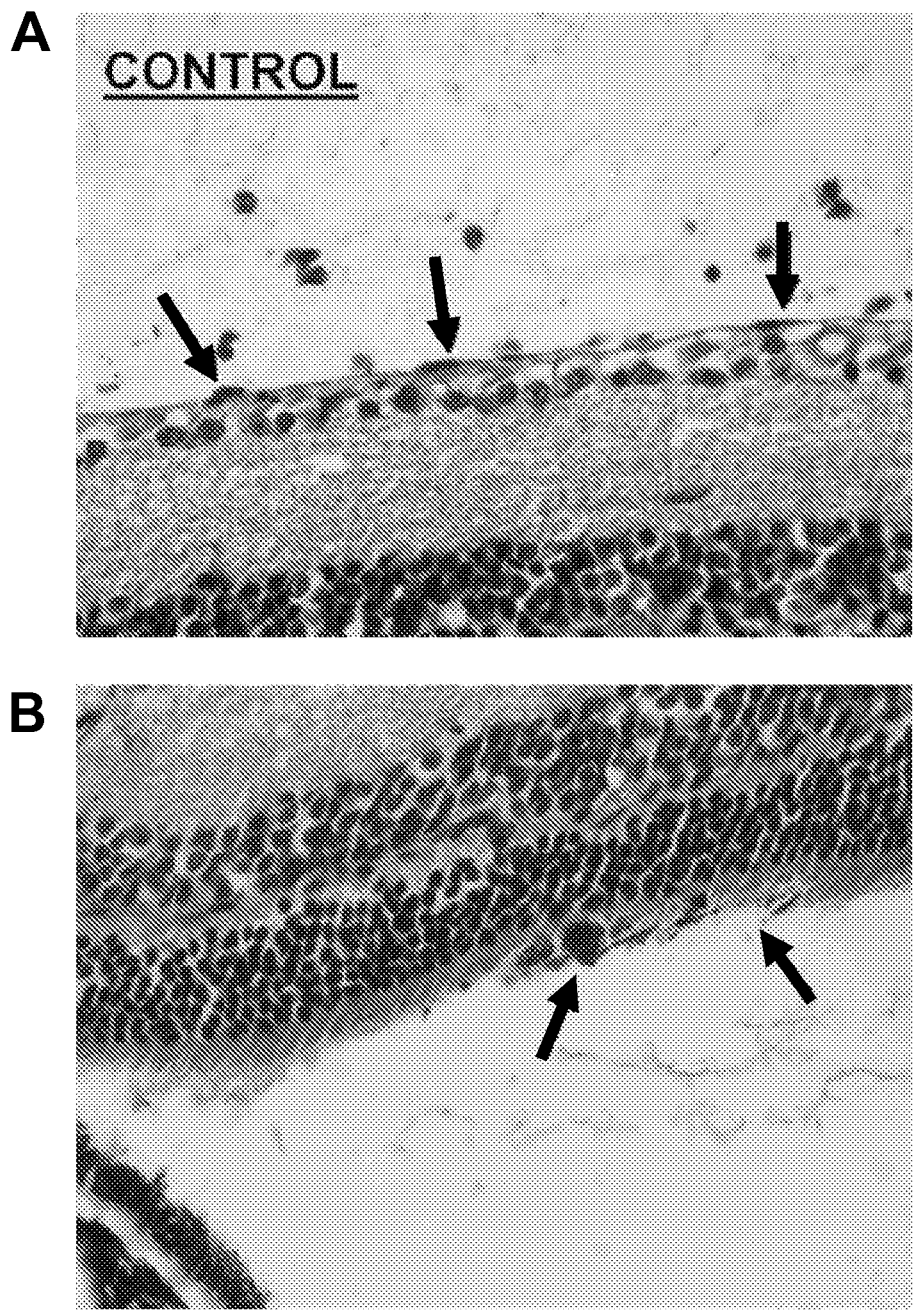
FIGS. 5A-5I are a series of photomicrographs of the eyes of a mouse model of proliferative vitreoretinopathy (PVR).
Figure 5:
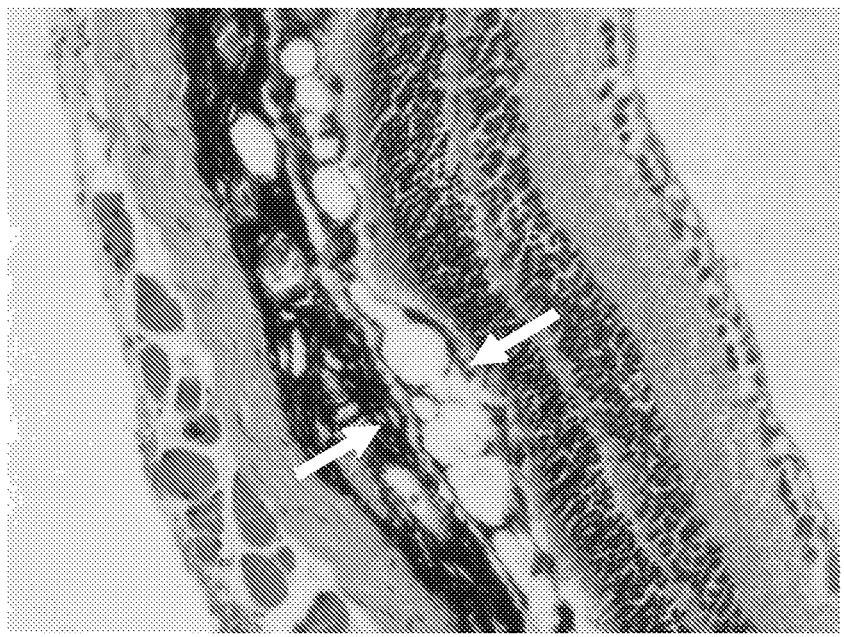
Figure 5:
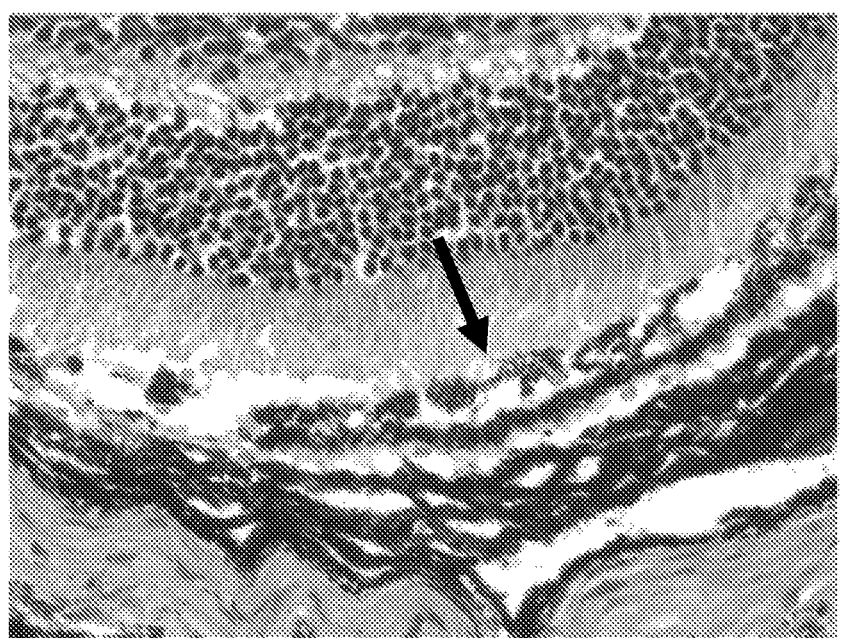
Figure 5:
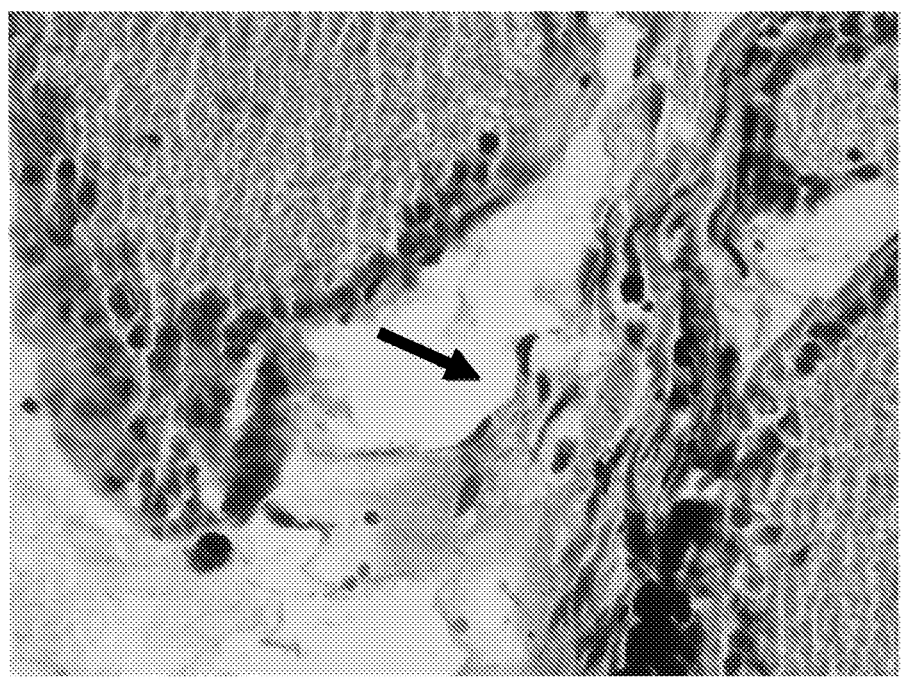
Figure 5:
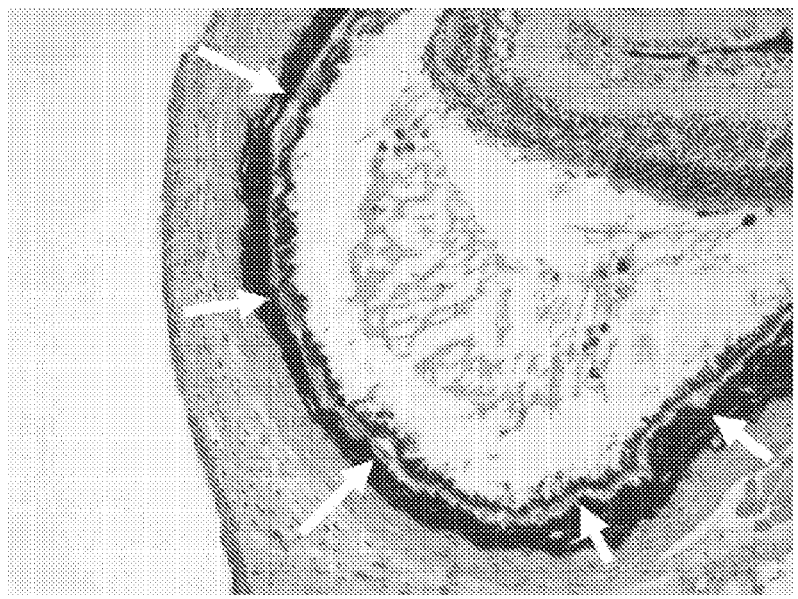
Figure 5:
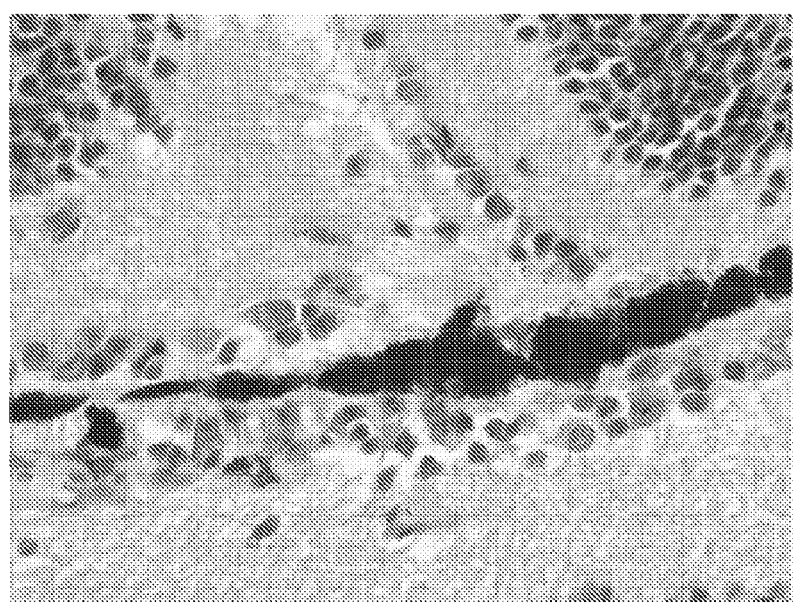
Figure 5:
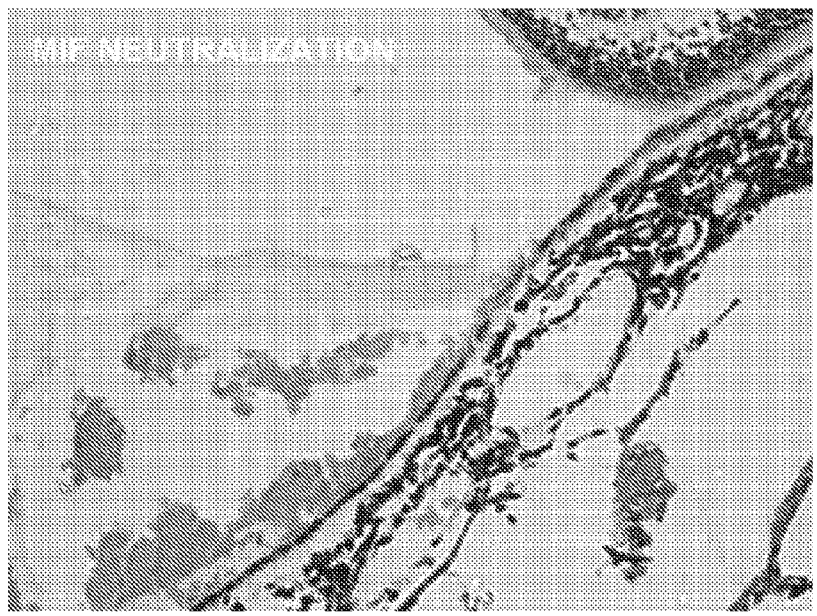
Figure 5:
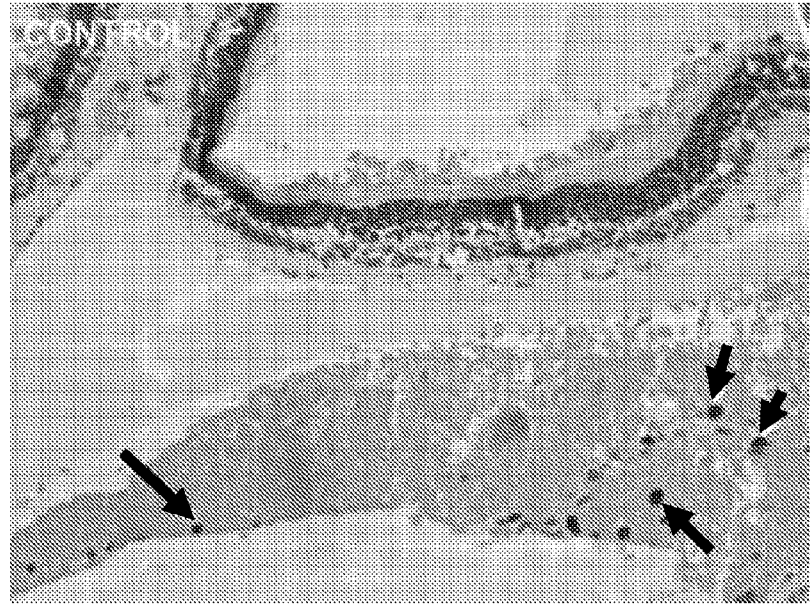

The results are shown in FIG. 5. Control animals that received subtenon DMSO/corn oil developed PVR as expected. Histological analyses demonstrated the development of preretinal (arrows in FIG. 5A) and subretinal (arrows in FIG. 5B) membranes. There were scattered RPE cells in the vitreous (above the arrows in FIG. 5A), and cells that attached on the retina (arrows in FIG. 5A) acquired a mesenchymal fusiform phenotype.

FIGS. 5C-5E show that in the control animals, RPE cells built up multiple layers in the subretinal space (between the arrows in FIG. 5C and indicated by the arrow in FIG. 5D), a feature associated with EMT, and also that epiretinal membranes formed by fusiform RPE cells (arrow in FIG. 5E) sometimes bridged the opposing retinal segments and exerted a transvitreal contractile force enough to detach the sensory retina.

By way of comparison, RPE cells in animals that received Compound 1 (see FIGS. 5F and 5G) maintained an epitheloid monolayer in the subretinal space and on the retina the preserved their cuboidal epitheliod morphology. No physical distortion related with the contraction of periretinal membranes was noted.

Figure 6:
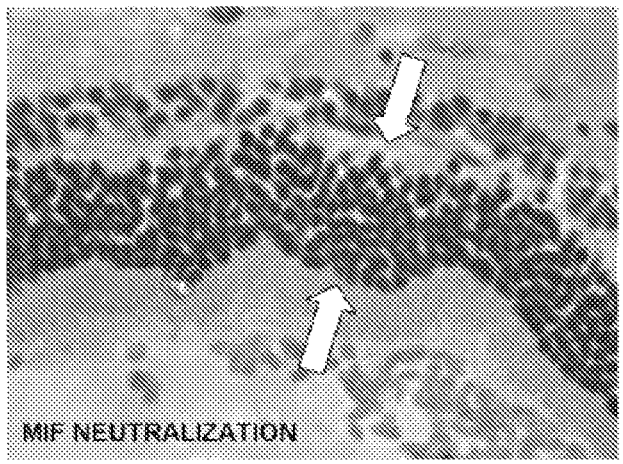
FIGS. 6A and 6B are photomicrographs of the eyes of rats either treated with Compound 1 (FIG. 6A) or with vehicle (FIG. 6B).
Figure 6:
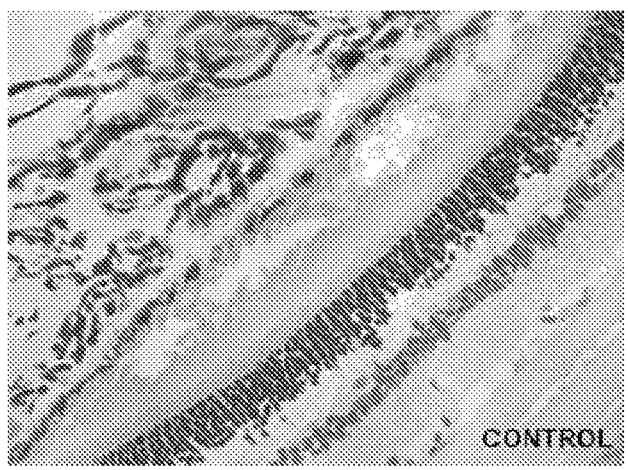

Similar experiments were also repeated using Brown Norway rats. In MIF neutralized animals (FIG. 5 H), RPE cells maintain their epitheloid morphology and did not invade the subretinal and/or intravitreal space. However, in control animals (FIG. 5 I) numerous RPE cells became migratory in the vitreous and started to form epiretinal membranes A better preservation of the photoreceptor cells in the detached retina of the animals treated with Compound 1 (FIG. 6A) compared with the controls (FIG. 6B) was also observed. This was evident with a thicker outer nuclear layer in Compound 1-treated animals (arrows in FIG. 6A). This effect could be attributed to an anti-apoptotic effect of MIF neutralization (see Arenberg et al., 2010).

Example 7

Figure 7:
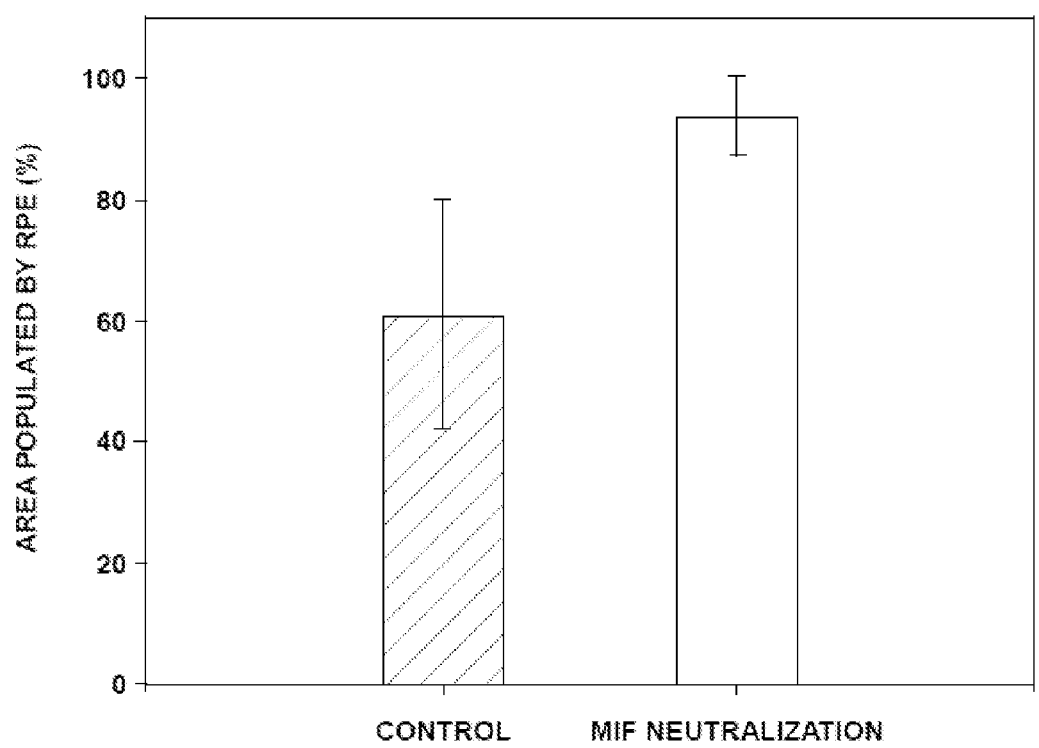
FIG. 7 is a bar graph showing surface coverage of RPE cells in a sodium iodate chemical debridement model of geographic atrophy. MIF neutralization with Compound 1 resulted in statistically significant greater surface coverage (p<0.001) when compared to vehicle alone (DMSO and corn oil).

Quantification of the Impact of MIF Neutralization on RPE Surface Coverage in a Chemical Debridement Model Sodium iodate was employed for chemical debridement of RPE to mimic geographic atrophy. Mice received $NaIO_3$ (25 mg/kg) intraperitoneally followed by subtenon injection of Compound 1 (500 μg in 5 μL) on day 7. Mice were sacrificed on Day 21 and the surface coverage by RPE cells was determined. As shown in FIG. 7, MIF neutralization with Compound 1 resulted in statistically significant greater surface coverage ($p<0.001$) when compared to vehicle alone (DMSO and corn oil).

Figure 8A:
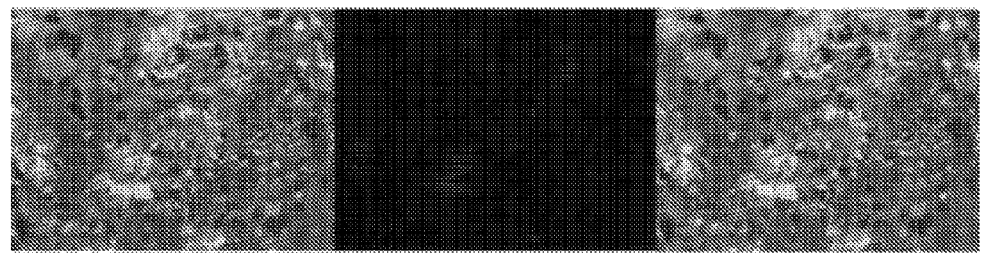
FIGS. 8A and 8B are fluorescence micrographs of the RPE surface coverage in the control mice and animals treated with the small molecule MIF inhibitor Compound 1, respectively. Three weeks after partial destruction of RPE cells, partial coverage of the debrided surface was observed in animals that received vehicle alone (i.e., DMSO and corn oil; see FIG. 8A). However, the RPE cells in animals that received small molecule MIF inhibitor Compound 1 proliferated at a higher rate; resurfaced the Bruch's membrane and formed an epithelial monolayer (see FIG. 8B).
Figure 8A:
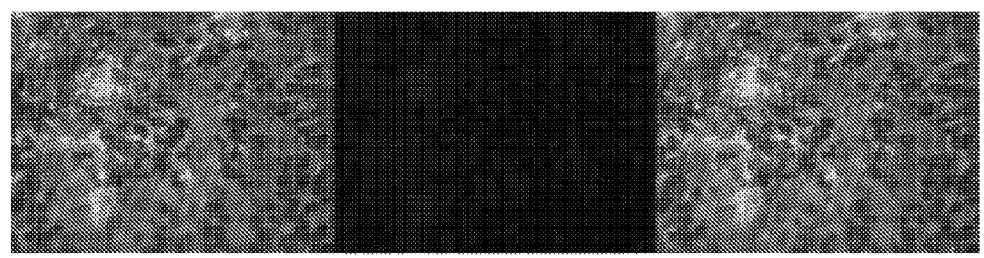
Figure 8B:
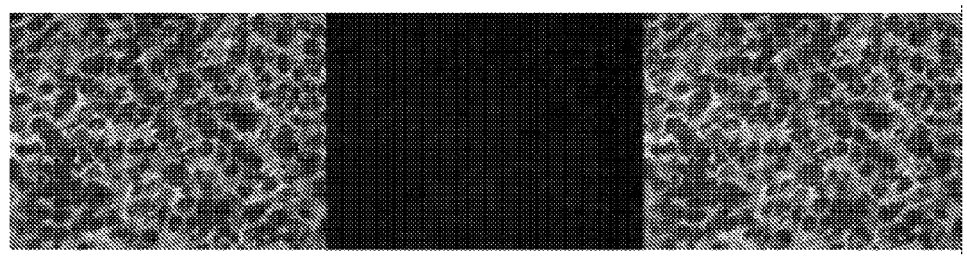
Figure 8B:
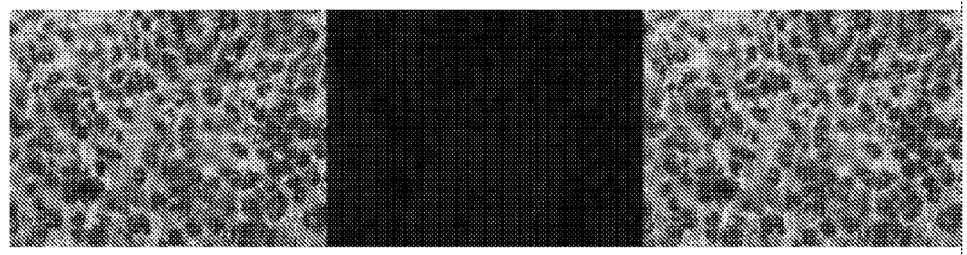

As shown in FIGS. 8A and 8B, partial coverage of the debrided surface was observed three weeks after partial destruction of RPE cells in animals that received vehicle alone (i.e., DMSO and corn oil; see FIG. 8A). However, the RPE cells in animals that received small molecule MIF inhibitor Compound 1 proliferated at a higher rate, resurfaced the Bruch's membrane, and formed an epithelial monolayer (see FIG. 8B).

Figure 9:
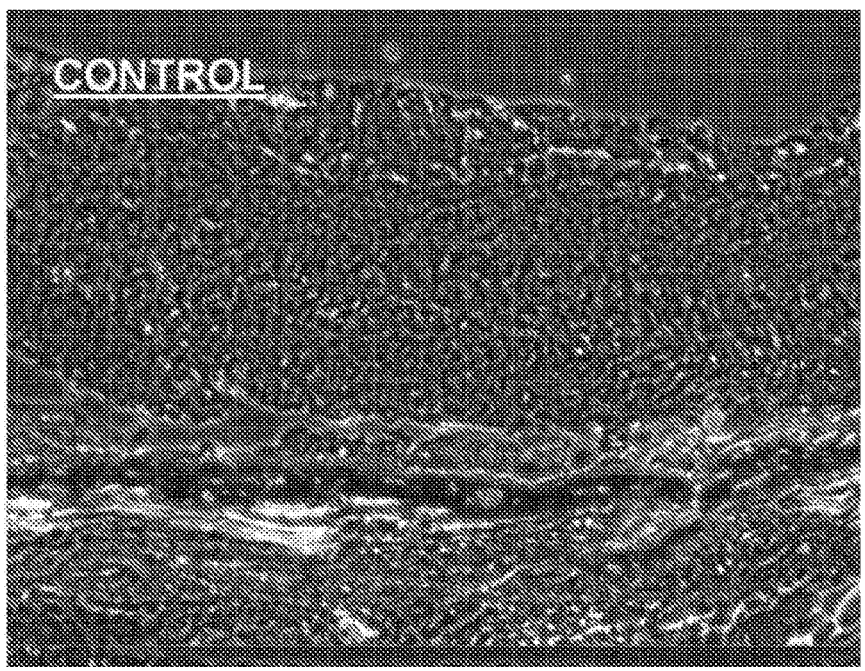
FIGS. 9A and 9B are photomicrographs of histological sections of paraffin-embedded eyes of the mice treated as set forth in FIG. 8.
Figure 9:
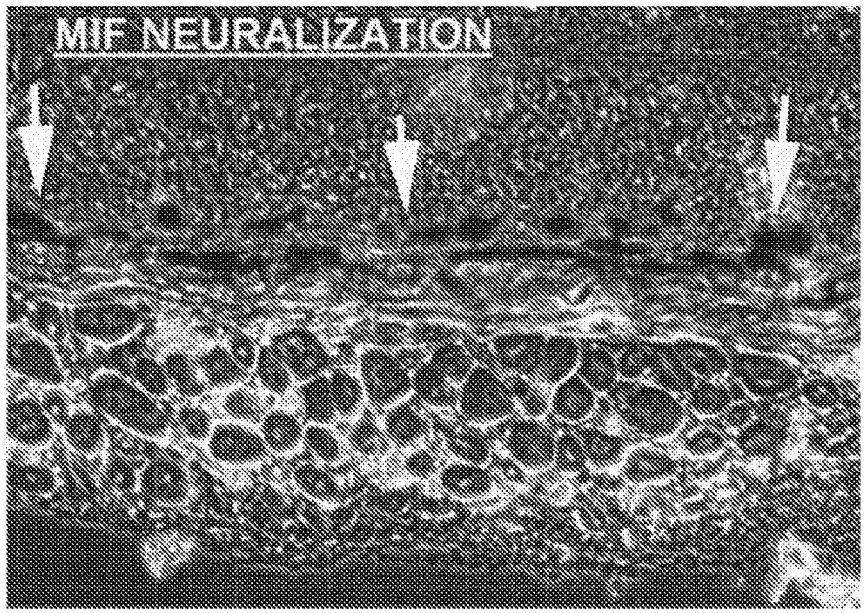

Histological analysis of the eyes of these animals confirmed these results a shown in FIGS. 9A and 9B. As shown in FIGS. 9A and 9B, better resurfacing of the denuded Bruch's membrane with RPE cells in animals treated with Compound 1 (arrows in FIG. 9B) was observed as compared to that seen in control animals (FIG. 9A).

In MIF neutralized animals, RPE cells established a monolayer in many places, whereas untreated control animals were fewer scattered cells.

Figure 10A:
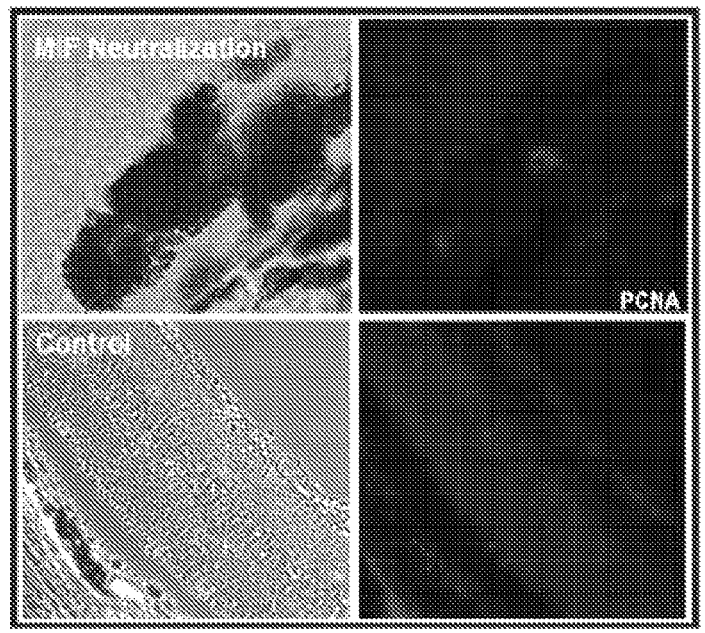
FIGS. 10A and 10B are a series of photomicrographs showing proliferating cell nuclear antigen (PCNA) and Terminal deoxynucleotidyl transferase dUTP nick end labeling (TUNEL) staining, respectively, of sections of ocular tissue isolated from mice that had been treated with the MIF inhibitor Compound 1 (top two panels of each Figure) as compared to vehicle control mice (lower two panels of each Figure).
Figure 10B:
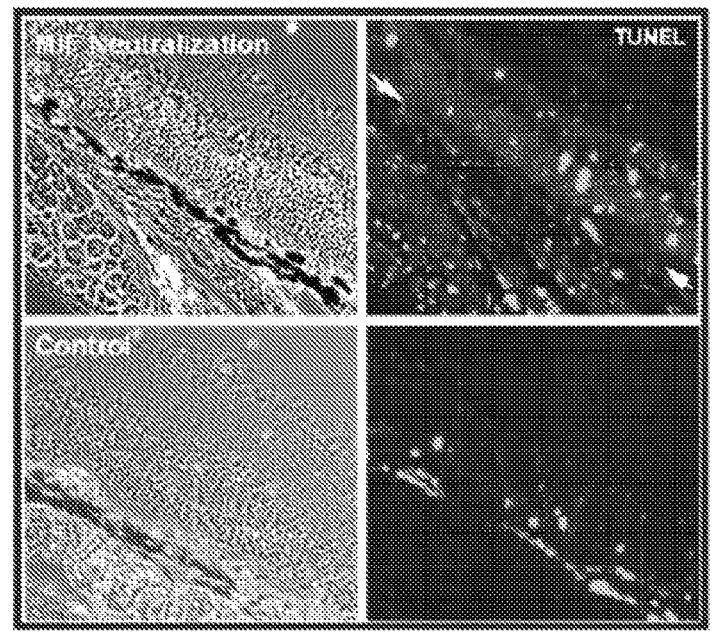

As shown in FIGS. 10A and 10B, PCNA and TUNEL staining revealed that better surface coverage in this model of geographic atrophy was the result of both increased cell proliferation and decreased apoptotic cell death in MIF neutralized cells.

Example 8

Figure 11A:
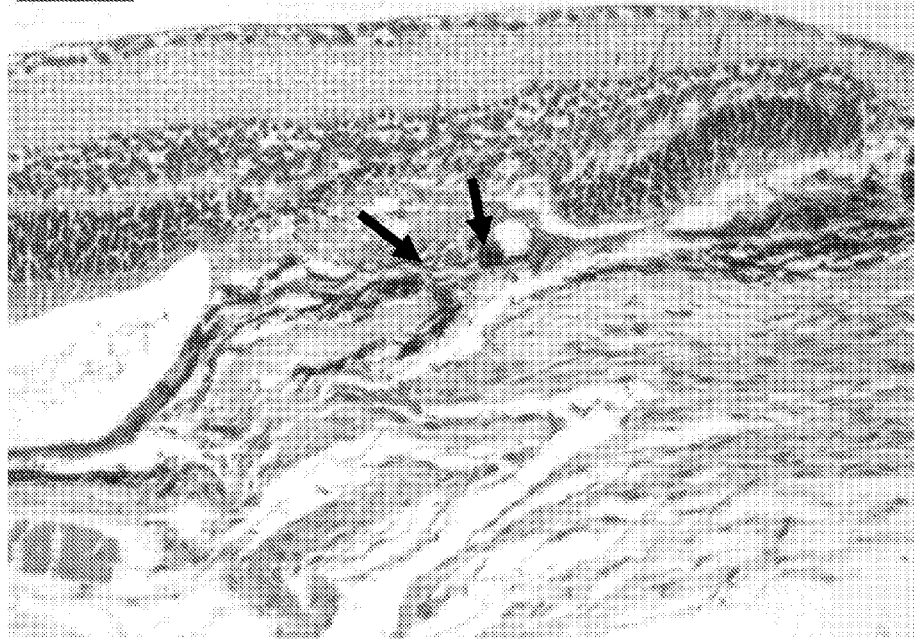
FIGS. 11A-11C are photomicrographs of histological examination of subretinal space choroidal neovascularization in vehicle control versus MIF neutralized mice subsequent to laser-induced retinal damage.
Figure 11B:
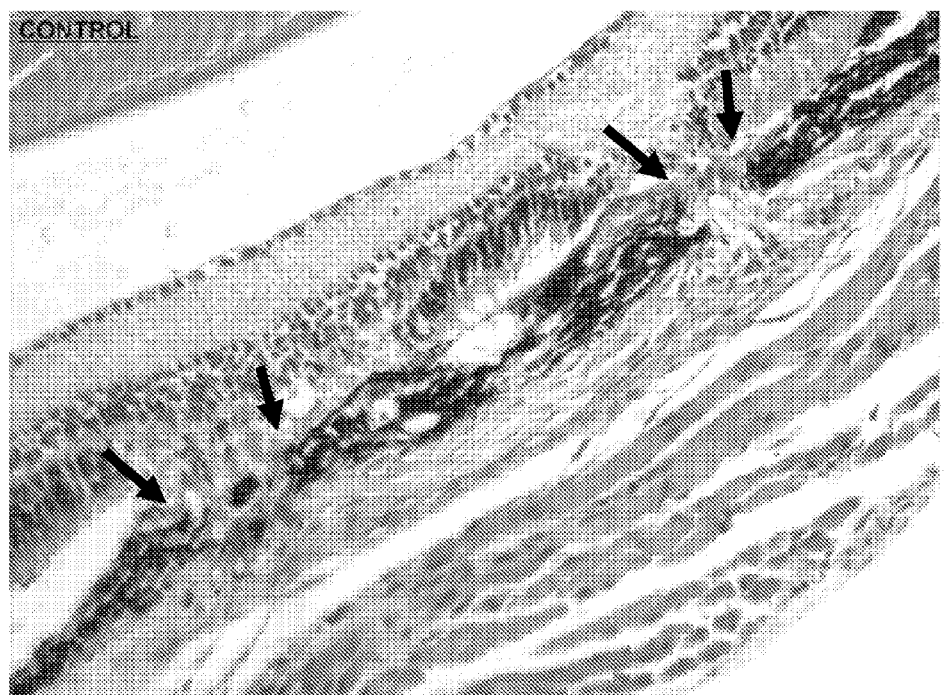
Figure 11C:

MIF Neutralization Induced RPE Growth Over Laser-Induced Spots and Resulted in Sealing of the Subretinal Space to Choroidal Neovascularization In control animals, choroidal new vessels gained access to the subretinal space through the breaks of the Bruch's membrane and RPE monolayer (arrows in FIGS. 11A and 11B). In MIF neutralized animals, RPE proliferated over the laser spot and sealed it off from neovascularization (arrows in FIG. 11C). This blocks the ingrowth of choroidal new vessels.

REFERENCES

All publications, patent applications, patents, and other references mentioned herein, including but not limited to those listed below, are incorporated by reference in their entireties to the extent that they supplement, explain, provide a background for, or teach methodology, techniques, and/or compositions employed herein. Some of the polynucleotide and polypeptide sequences disclosed herein are cross-referenced to GENBANK® Accession Numbers. The sequences cross-referenced in the GENBANK® database are expressly incorporated by reference as are equivalent and related sequences present in GENBANK® or other public databases. Also expressly incorporated herein by reference are all annotations present in the GENBANK® database entries associated with the sequences and GENBANK® Accession Numbers disclosed herein. In case of conflict, the present specification, including definitions, will control.

Abe et al. (2001) *J Immunol* 166:747-753.
Al-Abed & Van Patten (2011) *Future Med Chem* 3:45-63.
Arenberg et al. (2010) *Am J Respir Crit Care Med* 182:1030-1037.
Bacher et al. (1996) *Proc Natl Acad Sci USA* 93:7849-7854.
Bass (2001) *Nature* 411:428-429.
Batzer et al. (1991) *Nucleic Acid Res* 19:5081.
Bernstein et al. (2001) *Nature* 409:363-366.
Bloom et al. (1966) *Science* 153:80-82.
Bucala (1996) *FASEB J* 14:1607-1613.
Canadian Patent Application No. 2,359,180.
Chesney et al. (1999) *Mol Med* 5:181-191.
Cho et al. (2010) *Proc Natl Acad Sci USA* 107:11313-11318.
Churchill et al. (1975) *J Immunol* 115:781-785.
Cournia et al. (2009) *J Med Chem* 52:416-424.
Cunha et al. (1993) *J Immunol* 150:1908-1912.
David (1966) *Proc Natl Acad Sci USA* 56:72-77.
Donnelly et al. (1997) *Mol Med Today* 3:502-507.
Elbashir et al. (2001a) *Genes Dev* 15:188-200.
Elbashir et al. (2001b) *Nature* 411:494-498.
Fire (1999) *Trends Genet* 15:358-363.
Fire et al. (1998) *Nature* 391:806-811.
GENBANK® Accession Nos. NM_001032915; NM_001033608; NM_001077213; NM_001078655; NM_002415; NM_010798; NM_031051; NP_001028087; NP_001028780; NP_001070681; NP_001072123; NP_002406; NP_34928; NP_112313; XM_001489611; XP_001489661.
George et al. (1962) *Proc Soc Exp Biol Med* 111:514-521.
Hammond et al. (2000) *Nature* 404:293-296.
Hare et al. (2010) *Bioorg Med Chem Lett* 20:5811-5814
Hudson et al. (1999) *J Exp Med* 190:1375-1382.
Kithcart et al. (2010) *FASEB J* 24:4459-4466.
Leng et al. (2003) *J Exp Med* 97:1467-1476.
Liao et al. (2003) *J Biol Chem* 278:76-81.
McInnes et al. (1988) *J Exp Med* 167:598-611.
McLean et al. (2009) *Bioorg Med Chem Lett* 19:6717-6720.
Metz et al. (1997) *Adv Immunol* 66:197-223.
Mikayama et al. (1993) *Proc Natl Acad Sci USA* 90:10056-10060.
Mitchell et al. (1999) *J Biol Chem* 274:18100-18106.
Mitchell et al. (2002) *Proc Natl Sci USA* 99:345-350.
Nathan et al. (1971) *J Exp Med* 133:1356-1376.
Nathan et al. (1973) *J Exp Med* 137:275-288.
Nykanen et al. (2001) *Cell* 107:309-321.

Ogawa et al. (2000) *Cytokine* 12:309-314.
Ohtsuka et al. (1985) *J Biol Chem* 260:2605-2608.
Ouertatani-Sakouhi et al. (2010) *J Biol Chem* 285:26581-26598.
PCT International Publication Nos. WO 88/09344, WO 89/09622; WO 99/07409; WO 99/32619; WO 2000/01846; WO 2000/44895; WO 2000/44914; WO 2000/63364; WO 2001/04313; WO 2001/29058; WO 2001/36646; WO 2001/68836, WO 2001/75164; WO 2001/92513; WO 2002/055692; WO 2002/055693; WO 2002/044321; WO 2002/100332; WO 2003/006477; WO 2005/034952; WO 2007/112036; WO 2007/112015; WO 2007/140263; WO 2007/145888; WO 2009/085180; WO 2011/038234.
Petrenko & Moll (2005) *Mol Cell* 17:225-236.
Pozzi et al. (1992) *Cellular Immunol* 145:372-379.
Rice et al. (1998) *Ann Rep Med Chem* 33:243-252.
*Remington's Pharmaceutical Sciences,* 18th Edition, (1990) Gennaro (ed.) Mack Publishing Co., Easton, Pa., United States of America.
Rossolini et al. (1994) *Mol Cell Probes* 8:91-98.
Saika et al. (2004) *Lab Invest* 84:1245-1258.
Sakaue et al. (1999) *Mol Med* 5:361-371.
Shimizu et al. (1999) *Biochem Biophys Res Commun* 264: 751-758.
Swant et al. (2005) *J Biol Chem* 280:23066-23072.
Swope et al. (1999) *Rev Physiol Biochem Pharmacol* 139:1-32.
Thurman et al. (1985) *J Immunol* 134:305-309.
U.S. Patent Application Publication No. 2011/0009412.
U.S. Pat. Nos. 5,466,233; 5,877,293; 5,886,152; 6,054,297; 6,492,428; 6,645,493; 7,517,523; 7,648,959; 7,678,078; 7,883,717; 7,887,508; 7,931,909.
U.S. Provisional Patent Application Ser. Nos. 61/396,009; 61/419,404; 61/480,731.
Weiser et al. (1981) *J Immunol* 126:1958-1962.
Weiser et al. (1989) *Proc Natl Acad Sci USA* 86:7522-7526.
Weiser et al. (1991) *J Immunol* 147: 2006-2011.
Weiser et al. (1992) *Proc Natl Acad Sci USA* 89:8049-8052.
White et al. (2001) *J Immunol* 166:7549-7555.
White et al. (2003) *Clin Cancer Res* 9:853-860.
Wianny & Zernicka-Goetz (1999) *Nature Cell Biol* 2:70-75.
Winner et al. (2007) *Cancer Res* 67: 186-193.
Winner et al. (2008) *Cancer Res* 68:7253-7257.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for modulating eye damage, the method comprising administering to a subject an effective amount of a modulator of a migration inhibitory factor (MIF) polypeptide biological activity, wherein the eye damage is associated with a disease or disorder, damage incident to trauma including but not limited to blunt trauma, penetrating trauma, and trauma associated with ocular surgery, or a combination thereof, and further wherein the modulator has the following structure:

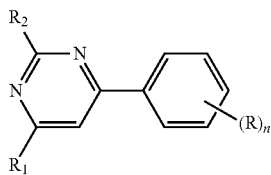

(I)

wherein:
  each R is independently H, halo, OH, alkyl, substituted alkyl, aryl, amino, or carboxyl;
  $R_1$ is H, halo, OH, alkyl, substituted alkyl, or aryl:
  $R_2$ is H, halo, OH, alkyl, substituted alkyl, aryl, or amino; and
  n is an integer from 0 to 5.

2. The method of claim 1, wherein the disease or disorder is selected from the group consisting of dry macular degeneration; wet macular degeneration; retinopathy of prematurity; background diabetic retinopathy; proliferative diabetic retinopathy; sickle cell retinopathy; other vascular retinopathies; intraocular scarring; proliferative vitreoretinopathy; autoimmune uveitis; autoimmune uveoretinitis; uveitis of various etiologies; dry eye syndrome with and without Sjogren's syndrome; blunt, penetrating, or perforating ocular trauma and related ocular pathologies; open angle glaucoma; and secondary glaucoma; as well as various structural disorders of the eye that require cell transplantation for tissue engineering.

3. The method of claim 1, wherein the damage incident to ocular surgery comprises scar formation and/or the administering step modulates a wound healing response in the eye on which the surgery was performed.

4. The method of claim 1, wherein the disease or disorder is dry macular degeneration or wet macular degeneration.

5. The method of claim 1, wherein $R_1$ is iodo, and optionally wherein $R_2$ is H and n is 0.

6. The method of claim 1, wherein the modulator is 4-iodo-6-phenylpyrimidine, 4-(2-fluorophenyl)-6-iodopyrimidine, or an analog or derivative thereof.

7. The method of claim 1, wherein the modulator comprises or encodes a nucleotide sequence that downregulates expression of a MIF gene product by RNA interference.

8. The method of claim 1, wherein the modulator comprises an anti-MIF antibody, or a fragment or derivative thereof.

9. The method of claim 1, wherein the MIF polypeptide is a mammalian MIF polypeptide.

10. The method of claim 9, wherein the MIF polypeptide:
  (i) is a human MIF polypeptide;
  (ii) comprises an amino acid sequence at least 95% identical to SEQ ID NO: 2; and/or
  (iii) is encoded by a human MIF genetic locus present on chromosome 22.

11. The method of claim 1, wherein the modulator is provided in a pharmaceutically acceptable composition, and optionally wherein the pharmaceutically acceptable composition is acceptable for use in a human.

12. The method of claim 11, wherein the pharmaceutically acceptable composition comprises a liposome and/or a nanoparticle in which the modulator is encapsulated and/or attached, optionally wherein the liposome and/or the nanoparticle comprises a targeting ligand that targets the liposome and/or the nanoparticle to the eye or a structure within the eye.

13. The method of claim 1, wherein the modulator of a migration inhibitory factor (MIF) polypeptide biological activity is 4-(2-fluorophenyl)-6-iodopyrimidine (Compound 1) or is 4-iodo-6-phenylpyrimidine (4-IPPI; Compound 2).

* * * * *